(12) United States Patent
Hamid et al.

(10) Patent No.: US 12,372,684 B2
(45) Date of Patent: Jul. 29, 2025

(54) NUMERICAL SIMULATION CAPABILITY FOR DETERMINING BLOCKAGES WITHIN A WELLBORE AND WELLBORE COMPLETION SETUPS

(71) Applicant: Saudi Arabian Oil Company, Dhahran (SA)

(72) Inventors: Osman Hamid, Houston, TX (US); Hussain AlBahrani, Al Qatif (SA)

(73) Assignee: Saudi Arabian Oil Company, Dhahran (SA)

( * ) Notice: Subject to any disclaimer, the term of this patent is extended or adjusted under 35 U.S.C. 154(b) by 578 days.

(21) Appl. No.: 17/752,317

(22) Filed: May 24, 2022

(65) Prior Publication Data
US 2023/0384479 A1 Nov. 30, 2023

(51) Int. Cl.
E21B 43/04 (2006.01)
E21B 47/04 (2012.01)
(Continued)

(52) U.S. Cl.
CPC .............. G01V 99/00 (2013.01); E21B 43/04 (2013.01); E21B 47/04 (2013.01); E21B 47/06 (2013.01);
(Continued)

(58) Field of Classification Search
CPC ........ G01V 99/00; G01V 20/00; E21B 43/04; E21B 47/04; E21B 47/06; E21B 47/08;
(Continued)

(56) References Cited

U.S. PATENT DOCUMENTS 2,848,469 A 8/1958 Harry et al.
3,200,106 A 8/1965 Dickson et al.
(Continued)

FOREIGN PATENT DOCUMENTS

CN 103377307 10/2013
EP 326720 8/1989
(Continued)

OTHER PUBLICATIONS

Abrams, "Mud design to mimimize rock impairment due to particle invasion" Journal of Petroleum Technology, May 1977, 29(5), 586-592, 7 pages.
(Continued)

Primary Examiner — Jeffrey P Aiello
(74) Attorney, Agent, or Firm — Fish & Richardson P.C.

(57) ABSTRACT

The systems and methods described in this specification relate to installing a wellbore completion setup of a wellbore based on a probability within a reservoir. The systems and methods measure one or more properties of the formation and receive data representing the one or more measured properties. The systems and methods use the one or more properties as input conditions to a finite element model of the wellbore. The systems and methods solve the finite element model to determine stresses of the formation surrounding the wellbore. The systems and methods determine a size of one or more rock fragments based on whether the determined stresses from the finite element model are greater than a threshold stress of a failure criterion. The systems and methods determine the probability, select the wellbore completion setup of the wellbore based on the bridging probability, and install the selected wellbore completion setup in the wellbore.

20 Claims, 18 Drawing Sheets

(51) Int. Cl.

| | |
|---|---|
| E21B 47/06 | (2012.01) |
| E21B 47/08 | (2012.01) |
| E21B 47/10 | (2012.01) |
| E21B 49/00 | (2006.01) |
| E21B 49/02 | (2006.01) |
| E21B 49/08 | (2006.01) |
| G01B 5/12 | (2006.01) |
| G01N 33/24 | (2006.01) |
| G01V 20/00 | (2024.01) |
| G01V 99/00 | (2024.01) |
| G06F 30/23 | (2020.01) |

(52) U.S. Cl.
CPC .............. *E21B 47/08* (2013.01); *E21B 47/10* (2013.01); *E21B 49/006* (2013.01); *E21B 49/02* (2013.01); *E21B 49/08* (2013.01); *G01N 33/24* (2013.01); *G01V 20/00* (2024.01); *G06F 30/23* (2020.01); *E21B 2200/20* (2020.05)

(58) Field of Classification Search
CPC ........ E21B 47/10; E21B 49/006; E21B 49/02; E21B 49/08; E21B 2200/20; E21B 43/00; E21B 47/00; E21B 47/09; E21B 49/00; G01N 33/24; G06F 30/23
USPC .............. 73/38, 152.46, 152.01; 166/250.01, 166/250.1, 308.1, 253.1; 175/57, 50; 702/6, 11, 12, 9, 188, 14, 13, 1, 2, 181, 702/189; 703/10, 2, 9, 7, 1
See application file for complete search history.

(56) References Cited

U.S. PATENT DOCUMENTS

| | | | |
|---|---|---|---|
| 3,750,768 | A | 8/1973 | Suman, Jr. et al. |
| 3,907,034 | A | 9/1975 | Suman, Jr. |
| 4,030,548 | A | 6/1977 | Richardson et al. |
| 4,081,030 | A | 3/1978 | Carpenter et al. |
| 4,287,946 | A | 9/1981 | Brieger |
| 4,589,504 | A | 5/1986 | Simpson |
| 4,776,410 | A | 10/1988 | Perkin et al. |
| 5,574,371 | A | 11/1996 | Tabanou et al. |
| 5,612,293 | A | 3/1997 | Swartwout et al. |
| 5,842,149 | A | 11/1998 | Harell et al. |
| 6,164,126 | A | 12/2000 | Ciglenec et al. |
| 6,180,571 | B1 | 1/2001 | Sifferman et al. |
| 7,114,562 | B2 | 10/2006 | Fisseler et al. |
| 8,457,940 | B2 | 6/2013 | Xi et al. |
| 8,548,783 | B2 | 10/2013 | Dean et al. |
| 8,962,535 | B2 | 2/2015 | Welton et al. |
| 9,353,305 | B1 | 5/2016 | Jiang et al. |
| 9,646,115 | B2 | 5/2017 | Frydman |
| 9,874,806 | B2 | 1/2018 | Takahara et al. |
| 9,920,233 | B2 | 3/2018 | Husein et al. |
| 10,000,690 | B2 | 6/2018 | Wu et al. |
| 10,088,725 | B2 | 10/2018 | Umezaki |
| 10,334,437 | B2 | 6/2019 | Katsman et al. |
| 10,400,570 | B2 | 9/2019 | Erge et al. |
| 10,597,959 | B2 | 3/2020 | Rao et al. |
| 10,725,012 | B2 | 7/2020 | Lander et al. |
| 10,982,124 | B2 | 4/2021 | AlBahrani et al. |
| 11,261,730 | B2 | 3/2022 | AlBahrani et al. |
| 2004/0221985 | A1 | 11/2004 | Hill et al. |
| 2005/0149307 | A1* | 7/2005 | Gurpinar ................ E21B 43/00 703/10 |
| 2006/0200328 | A1 | 9/2006 | Guo et al. |
| 2008/0070805 | A1 | 3/2008 | Munoz et al. |
| 2009/0084554 | A1 | 4/2009 | Williamson et al. |
| 2010/0071957 | A1 | 3/2010 | Huang et al. |
| 2011/0153296 | A1 | 6/2011 | Sadlier et al. |
| 2011/0168395 | A1 | 7/2011 | Welton et al. |
| 2011/0312857 | A1 | 12/2011 | Amanullah et al. |
| 2012/0123756 | A1 | 5/2012 | Wang et al. |
| 2013/0261032 | A1 | 10/2013 | Ladva et al. |
| 2014/0032192 | A1 | 1/2014 | Zamora et al. |
| 2014/0116776 | A1 | 5/2014 | Trent et al. |
| 2014/0122035 | A1 | 5/2014 | Dean et al. |
| 2014/0151042 | A1 | 6/2014 | Faugerstrom et al. |
| 2014/0190695 | A1 | 7/2014 | van Zanten et al. |
| 2014/0231146 | A1 | 8/2014 | Nguyen |
| 2015/0041120 | A1* | 2/2015 | Gumarov ................ E21B 47/10 166/250.1 |
| 2015/0191640 | A1 | 7/2015 | Lee et al. |
| 2016/0076357 | A1 | 3/2016 | Hbaeib et al. |
| 2018/0051548 | A1 | 2/2018 | Liu et al. |
| 2018/0119535 | A1 | 5/2018 | Shen et al. |
| 2020/0072026 | A1* | 3/2020 | Ray .......................... G01V 9/00 |

FOREIGN PATENT DOCUMENTS

| | | |
|---|---|---|
| WO | 2011083182 | 7/2011 |
| WO | 2013189842 | 12/2013 |

OTHER PUBLICATIONS

Adham, "Geomechanics model for wellbore stability analysis in Field 'X', North Samatra Basin," retrieved from URL <https://mountainscholar.org/bitstream/handle/11124/17O314/Adham_mines_0O52N_llO59.pdf?sequence=1>, Jan. 1, 2016, 121 pages.

Albukhari et al., "Geomechanical Wellbore Stability Analysis for the Reservoir Section in J-NC186 Oil Field," retrieved from URL <https://www.onepetro.org/download/conference-paper/ISRM-TUNIROCK-2018-22?id=conference-paper/ISRM-TUNIROCK-2018-22>, retrieved on Oct. 14, 2019, published Mar. 31, 2018, 15 pages.

Al-Haidary, "Wellbore Stability Assessment in a Shale Formation," retrieved from URL <http://eprints.kfupm.edu.sa/139181/1/Wellbore_Stability_Assessment_in_a_shale_formation_Saleh_AlHaidary.pdf>, retrieved on Oct. 14, 2019, published May 1, 2014, 136 pages.

Alsubaih, "Shale instability of deviated wellbores in southern Iraqi frields," retrieved from URL <http://scholarsmine.mst.edu/cgi/viewcontent.cgi?article=8544&context=masters_theses>, retrieved on Oct. 14, 2019, published Jan. 1, 2016, 129 pages.

Kosset, "Wellbore integrity analysis for wellpath optimization and drilling risks reduction: the vaca muerta formation in neuquen basin," retrieved from URL <https://mountainscholar.org/bitstream/handle/11124/464/Kosset_mines_0O52N_1O469.pdf?sequence=l&isAllowe3=y>, published Jan. 1, 2014, 131 pages.

Lang et al., "Wellbore Stability Modeling and Real-Time Surveillance for Deepwater Drilling to Weak Bedding Planes and Depleted Reservoirs, " SPE, Mar. 1, 2011, 18 pages.

Li et al., "Pore-pressure and wellbore-stability prediction to increase drilling efficiency," Journal of Petroleum Technology, Feb. 28, 2012, 4 pages.

Liu et al., "In situ deformation analysis of a fracture in coal under cyclic loading and unloading," Energies, Oct. 2021, 14(20):6474, 16 pages.

Tan et al., "Wellbore Stability of Extended Reach Wells in an Oil Filed in Sarawak Basin, South China Sea," SPE Proceedings, XX, XX, SPE88609, Oct. 18, 2004, 11 pages.

Tutuncu et al., "Annual Meeting Selections. Integrated Wellbore-Quality and Risk-Assessment Study Guides Successful Drilling in Amazon Jungle," Geophysics, Society of Exploration Geophysics, vol. 71, No. 6, Jan. 1, 2006, 7 pages.

Voorn et al., "Porosity, permeability and 3D fracture network characterisation of dolomite reservoir rock samples," Journal of Petroleum Science and Engineering, Mar. 2015, 127:270-285, 39 pages.

* cited by examiner

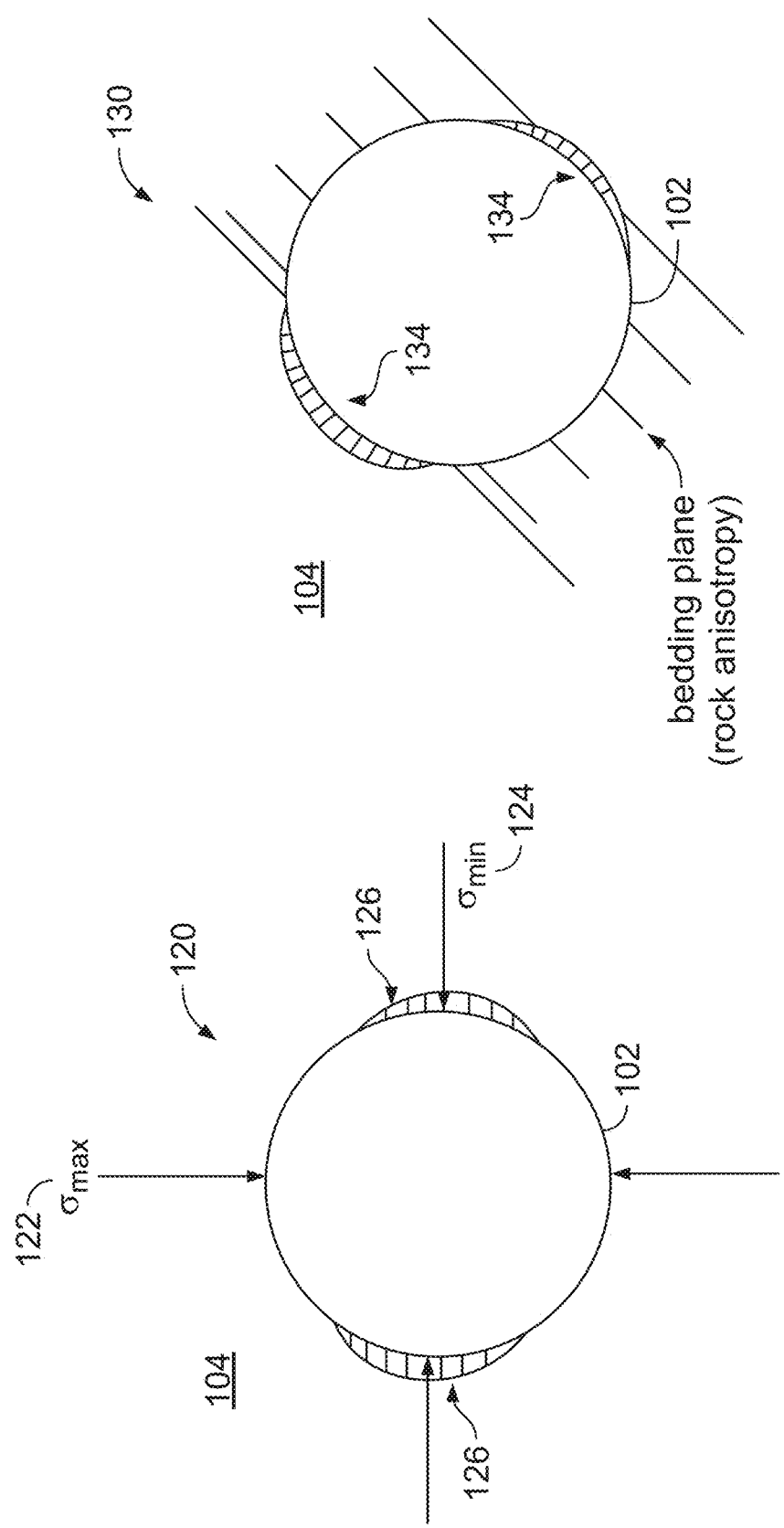

NUMERICAL SIMULATION CAPABILITY FOR DETERMINING BLOCKAGES WITHIN A WELLBORE AND WELLBORE COMPLETION SETUPS

TECHNICAL FIELD

The present disclosure describes systems and methods for determining blockage probabilities within a wellbore and/or a reservoir and determining a wellbore completion setup based on the blockage probabilities.

BACKGROUND

Open-hole completion setups are often less expensive to install in wells compared to cased and perforated completion setups. However, wells with an open-hole completion setup are more susceptible to production interruptions due to reservoir blockages and sand entering the well compared to cased and perforated wells. In some examples, rock fragments can separate from the formation surrounding the well and accumulate within the reservoir, causing a blockage. In wells with an open-hole completion setup, the rock fragments can disintegrate and be carried with the reservoir fluid as the reservoir fluid flows through the well to the ground surface. Flowing rock fragments can cause abrasive damage to surface pipelines and production facilities. In some cases, the rock fragments can accumulate within the reservoir and/or the well and cause a restriction of reservoir fluid flow to the ground surface. In some cases, the restrictions can be severe and even be a complete blockage where substantially no reservoir fluid is able to pass to the ground surface. Such restrictions and/or blockages can negatively affect well production.

SUMMARY

The systems and methods described in this disclosure use a three-dimensional finite element model of a wellbore and the formation surrounding the wellbore to predict whether a reservoir is likely to become restricted. The systems and methods determine whether a portion of the formation is likely to separate from the formation based on the stresses predicted by the finite element model as a result of the loading and production history of the wellbore. The systems and methods determine the size of the rock fragment based on the size of the finite elements that are predicted to fail based on the predicted stresses. The systems and methods determine the probability that the predicted rock fragments from the finite element model will accumulate and form at least one restriction in the reservoir.

The systems and method described in this disclosure use the fluid properties of fluid within the wellbore and the solid properties of the formation surrounding the wellbore when determining whether a reservoir is likely to become restricted. For example, the settling velocity of the rock fragments within the reservoir is used to determine how quickly the rock fragments flow through the reservoir. This information is used with diameter predictions from the finite element model to determine how likely the rock fragments might settle and form a restriction within the wellbore. The height of the rock fragments assembling in a direction perpendicular to the flow of the wellbore is used as part of this determination. The location in the wellbore and the point in time when the rock fragments restrict or block the flow passage is determined using a bridging criterion.

In some examples, the systems and methods determine a completion setup based on the probability that the predicted rock fragments will form at least one restriction. For example, the systems and methods determine that an open-hole completion setup should be installed in wellbores associated with a low probability, and a cased and perforated completion setup should be installed in wellbores associated with a high probability. In turn, the systems and methods install the selected completion setup in the wellbore to reduce the likelihood of restrictions and/or blockages forming.

Some systems and methods for installing a wellbore completion setup of a wellbore include one or more of the following features. Some systems and methods measure one or more properties of a formation surrounding the wellbore and measure one or more properties of a fluid within the wellbore. Some systems and methods receive, at a processor, data representing the one or more measured properties of the formation and data representing the one or more properties of a fluid within the wellbore. Some systems and methods use, by the processor, the one or more properties of the formation and the one or more properties of the fluid as input conditions to a three-dimensional finite element model of the wellbore. Some systems and methods solve, by the processor, the finite element model to determine stresses of the formation, wherein solving the finite element model includes evaluating a failure criterion for at least one finite element of the finite element model. Some systems and methods determine, by the processor, a size of one or more rock fragments based on whether the determined stresses from the finite element model are greater than a threshold stress of the failure criterion such that the one or more rock fragments are predicted to separate from the formation. Some systems and methods determine, by the processor, a probability that the one or more rock fragments form at least one restriction in a reservoir based on the size of the one or more rock fragments and the one or more measured properties of the formation. Some systems and methods select, by the processor, the wellbore completion setup of the wellbore based on the probability that the one or more rock fragments form at least one restriction in the reservoir. Some systems and methods install the selected wellbore completion setup in the wellbore.

Some systems and methods include one or more of the following features.

In some implementations, measuring the one or more properties of the formation includes measuring, using a caliper log, a diameter of the wellbore as a function of depth within the wellbore. Some systems and methods determine, by the processor using at least one result of the finite element model, a predicted diameter of the wellbore as a function of depth based on the determined size of the one or more rock fragments; compare the measured diameter of the wellbore to the predicted diameter of the wellbore; and validate, by the processor, the finite element model based on the comparison. In some examples, the wellbore includes at least two laterals and measuring the diameter of the wellbore as the function of depth within the wellbore includes measuring the diameter of the wellbore as the function of depth within each of the at least two laterals of the wellbore.

In some implementations, measuring the one or more properties of the formation includes extracting a core sample from the formation; and determining, by testing the extracted core sample, a compressive strength of the formation. Some systems and methods determine, by the processor, one or more parameters of the failure criterion based on the determined compressive strength of the formation.

In some implementations, the finite element model includes at least one plasticity model and solving the finite element model includes determining the stresses of the formation based on the at least one plasticity model while being subject to the failure criterion.

In some implementations, determining the size of the one or more rock fragments includes: determining, by the processor, one or more regions of the formation from the finite element model where the determined stresses exceed the threshold stress; determining, by the processor, a size for each of the one or more regions of the formation where the determined stresses exceed the threshold stress; determining the size of the one or more rock fragments based on the determined size of the one or more regions; and determining a diameter of the wellbore based on the determined size of the one or more regions. In some implementations, determining the size for each of the one or more regions of the formation includes: retrieving one or more coordinates of each node of the finite element model where the stresses exceed the threshold stress; determining a polygon that encapsulates each of the one or more coordinates of each node of the finite element model where the stresses exceed the threshold stress; determining the size of the one or more rock fragments based on one or more dimensions of the determined polygon; and determining the diameter of the wellbore based on a size of the determined polygon.

In some implementations, measuring the one or more properties of the formation includes measuring, using a caliper log, a diameter of the wellbore, wherein determining the size of the one or more rock fragments includes determining an effective diameter of each of the one or more rock fragments, and wherein determining the probability includes determining the probability by comparing the effective diameters of each of the one or more rock fragments from the finite element model to the measured diameter of the wellbore. Some systems and methods determine, by the processor, a mean diameter of the wellbore based on the measured diameter of the wellbore, wherein comparing the effective diameters from the finite element model to the measured diameter includes comparing the diameters from the finite element model to the determined mean diameter of the wellbore.

Some systems and methods determine, by the processor, a statistical distribution of the effective diameters of the one or more rock fragments based on each of the one or more rock fragments from the finite element model, wherein comparing the effective diameters from the finite element model to the measured diameter includes comparing the statistical distribution of the diameters of the one or more rock fragments to the measured diameter of the wellbore. Some systems and methods determine, by the processor, a number of occurrences within a pre-determined percentile range of the statistical distribution, wherein comparing the statistical distribution of the effective diameters of the one or more rock fragments to the measured diameter of the wellbore includes comparing the number of occurrences to the measured diameter of the wellbore. In some implementations, determining the probability includes: determining that the probability is greater than a restriction threshold when the number of occurrences within the pre-determined percentile range of the statistical distribution is greater than or equal to a pre-determined fraction of the maximum measured diameter of the wellbore, wherein the probability being greater than the restriction threshold is indicative that at least one restriction is likely to occur; and determining that the probability is less than the restriction threshold when the number of occurrences within the pre-determined percentile interval of the statistical distribution is less than the pre-determined fraction of the maximum measured diameter of the wellbore, wherein the probability being less than the restriction threshold is indicative that at least one restriction is unlikely to occur.

Some systems and methods determine, by the processor, a settling velocity of the one or more rock fragments based on the one or more properties of the fluid within wellbore, wherein determining the probability includes determining that the probability is greater than a restriction threshold when the determined settling velocity of the one or more rock fragments is less than a settling velocity threshold, wherein the probability being greater than the restriction threshold is indicative that at least one restriction is likely to occur.

Some systems and methods determine a height of a rock fragment bed accumulation based on an effective diameter of each of the one or more rock fragments. In some examples, a direction of the height is perpendicular to a longitudinal axis of the wellbore.

In some implementations, determining the probability includes: determining, by the processor, a flow regime of the fluid based on the one or more properties of the fluid within wellbore, the determined flow regime being either turbulent or laminar; and determining, by the processor, a drag coefficient of the one or more rock fragments based on the one or more properties of the fluid within wellbore and the determined flow regime.

In some implementations, determining the probability includes: determining a predicted cumulative volume of sand produced as a function of a bottom hole pressure of the wellbore based on the determined stresses from the finite element model; and determining the probability based on the predicted cumulative volume of sand produced.

In some implementations, selecting the completion setup of the wellbore includes: selecting the completion setup to be an open-hole completion when the probability is less than a first threshold; selecting the completion setup to be an open-hole with a gravel pack completion setup when the probability is between the first threshold and a second threshold; and selecting the completion setup to be a cased and perforated completion setup when the probability is greater the second threshold.

The systems and methods described in this specification provide one or more of the following advantages.

By installing the selected completion setup in the wellbore, expensive and unnecessary completion setups are avoided. For example, if the systems and methods determine that there is a relatively low probability that rock fragments will form a restriction (for example, in wells having a low production rate surrounded by tough rock), then the systems and methods elect an open-hole completion setup to reduce expense. If the systems and methods determine is a relatively high probability that rock fragments will form a restriction (for example, wells having a high production rate surrounded by fragile rock), then the systems and methods select a cased and perforated completion setup to reduce the likelihood of a restriction developing in the reservoir.

By installing the selected completion setup in the wellbore and pumping reservoir fluid through the well, abrasive effects of sand production on pipelines and surface facilities are reduced or avoided compared to wells that use an incorrect completion setup.

By installing the selected completion setup in the wellbore and pumping reservoir fluid through the well, non-productive time (NPT) is reduced. For example, reducing the probability that restrictions and/or blockages will develop means that wellbore cleaning while drilling is reduced. Wellbore cleaning generally requires the well to temporarily stop production so that then cleaning can be performed, which leads to undesirable non-productive time (NPT).

By using a three-dimensional finite element model to predict the rock fragments, the systems and methods can predict rock fragments accurately. For example, the three-dimensional finite element model simulates both solid aspects (for example, the formation) and fluid aspects (for example, the fluid within the reservoir), which results in a more accurate prediction of rock fragments compared to finite element models that do not consider these fluid aspects.

By using a three-dimensional finite element model to predict the rock fragments, the systems and methods can predict rock fragments in a time-dependent manner. For example, the finite element models consider the production or injection of flow (for example, pore pressure change over time) and loading history (for example, drilling and completion fluid weights).

By using a three-dimensional finite element model to predict the rock fragments, the systems and methods can account for material plasticity, which increases the accuracy of the prediction compared to the method that does not account for material plasticity.

By using a three-dimensional finite element model to predict the rock fragments, the systems and methods can solve for geo-mechanical solutions that would otherwise be difficult, if not intractable to solve analytically.

By using a three-dimensional finite element model to predict the rock fragments, the systems and methods can solve for rock fragments and restrictions in real-time and/or while-drilling of a physical well. For example, the finite element model can guide engineers while drilling the well to reduce the probability of forming rock fragments.

By using a three-dimensional finite element model to predict the rock fragments, the systems and methods predict the geometrical variation in flow path channel size (for example, the wellbore actual or caliper-based diameter).

By using a three-dimensional finite element model to predict the rock fragments, the systems and methods predict the volume of the failed rock fragments and use this volume to predict the sand production rate.

By using a three-dimensional finite element model to predict the rock fragments, the systems and methods use a sand accumulation and bridging condition to predict the parameters at which production blockage could occur. The systems and methods use these parameters to avoid selecting the completion setup.

By using a three-dimensional finite element model to predict the rock fragments, the systems and methods use logging data (for example, both wireline and logging while drilling) in addition to core-based measurements (for example, to reveal formation rock heterogeneity properties) as inputs to the finite element model to increase the accuracy of the model predictions.

The details of one or more embodiments of these systems and methods are set forth in the accompanying drawings and the description below. Other features, objects, and advantages of these systems and methods will be apparent from the description and drawings and from the claims.

DESCRIPTION OF DRAWINGS

FIG. 2A is a schematic of in-situ stresses of a formation and regions where cavings and rock fragments can develop. FIG. 2B is a schematic of the bedding plane anisotropy of a formation and regions where cavings and rock fragments can develop.

FIG. 8A is a plot of two disconnected regions surrounding the wellbore where cavings are predicted to develop, and FIG. 8B is a plot of a continuous region surrounding the wellbore where cavings are predicted to develop.

FIG. 14A is based on based on the Lade failure criterion, FIG. 14B is based on the Mogi failure criterion and FIG. 14C is based on the Mohr failure criterion.

FIG. 15A is based on based on the Lade failure criterion, FIG. 15B is based on the Mogi failure criterion, and FIG. 15C is based on the Mohr failure criterion.

Like reference symbols in the various drawings indicate like elements.

DETAILED DESCRIPTION

The systems and methods described in this disclosure use a three-dimensional finite element model of a wellbore and the formation surrounding the wellbore to predict whether a reservoir is likely to become restricted. The systems and methods determine whether a portion of the formation is likely to separate from the formation based on the stresses predicted by the finite element model as a result of the loading and production history of the wellbore. The systems and methods determine a size of the rock fragment based on the size of the finite elements that are predicted to fail based on the predicted stresses. The systems and methods determine the probability that the predicted rock fragments from the finite element model will accumulate and form at least one restriction in the reservoir.

The systems and method described in this disclosure use fluid properties of a fluid within the wellbore and the solid properties of the formation surrounding the wellbore when determining whether a reservoir is likely to become restricted. For example, the settling velocity of the rock fragments within the reservoir is used to determine how quickly the rock fragments flow through the reservoir. This information is used with diameter predictions from the finite element model to determine how likely the rock fragments might settle and form a restriction within the wellbore. The height of the rock fragments assembling in a direction perpendicular to the flow of the wellbore is used as part of this determination. The location in the wellbore and the point in time when the rock fragments restrict or block the flow passage is determined using a bridging criterion.

Figure 1:
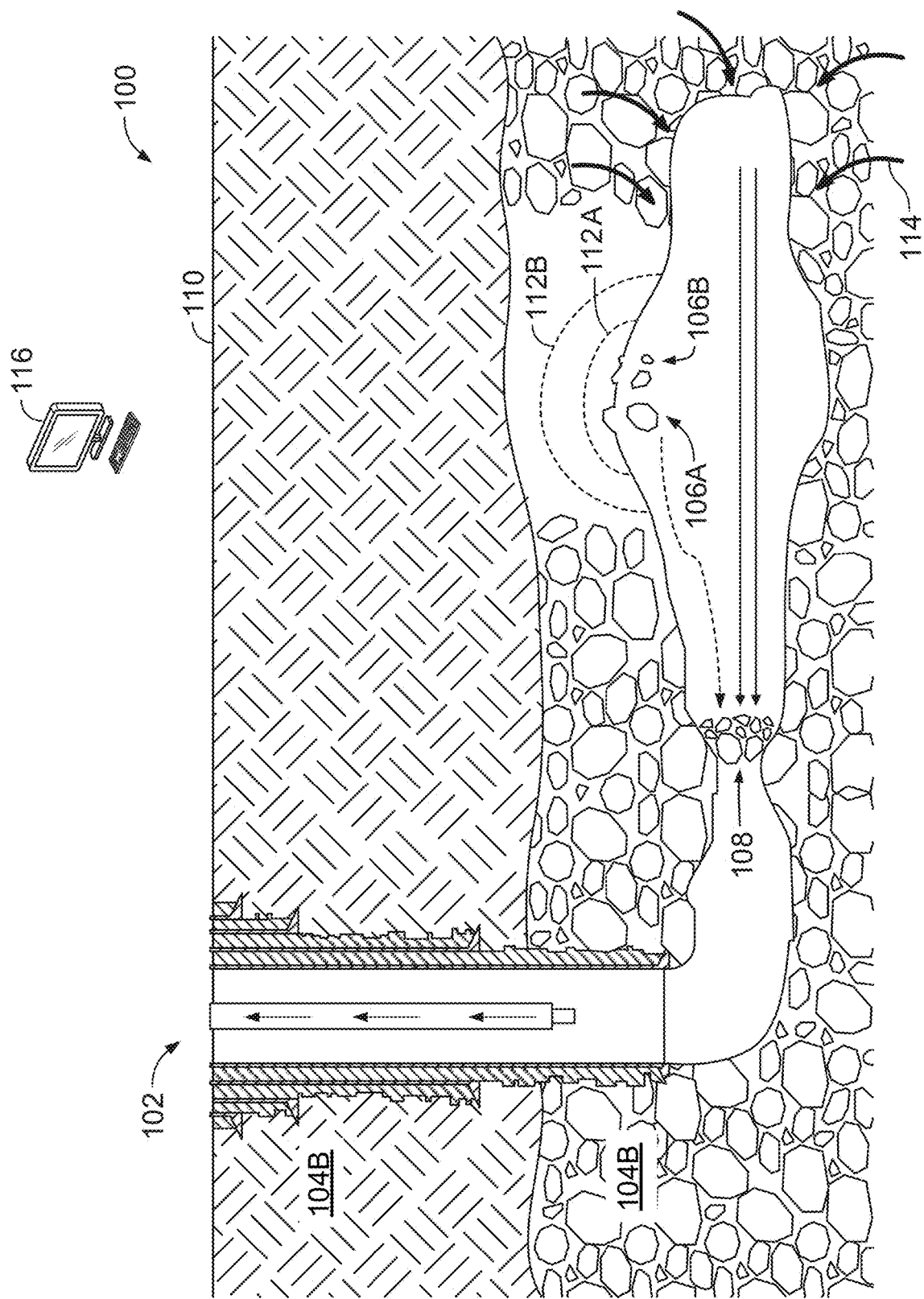
FIG. 1 is an illustration of a flow restriction in a reservoir caused by an accumulation of formation fragments.

FIG. 1 is an illustration of an environment 100 with a wellbore 102. The wellbore has been drilled through a formation 104 which includes a first formation layer 104A and a second formation layer 104B. These two formation layers 104A, 104B (collectively referred to as "formation 104") can have different properties. For example, the first formation layer 104A can represent a dense non-porous rock such as sandstone. In environment 100, the second formation layer 104B represents a porous reservoir rock occupied by oil 114 which permeates through the reservoir rock and through and/or around crevices of the reservoir rock and represents a reservoir of oil 114.

The wellbore 102 includes a vertical section that extends from the ground surface 110 into the reservoir of oil 114, and a horizontal (for example, lateral) section that extends into the reservoir of oil 114. Wellbores having different orientations (for example, two or more laterals, no laterals, a deviation, etc.) can also be used.

The formation 104 is subject to in-situ stresses produced by overburden above the formation 104 and underburden below the formation 104. These in-situ stresses apply compressive stresses to the formation 104. In some cases, one or more regions of the formation 104 are subject to compressive stresses that exceed the compressive strength of formation 104. This can cause a portion of the formation 104 to fail and break-free from the surrounding formation 104. The failed and broken-free formation 104 forms rock fragments 106A, 106 (collectively "rock fragments 106").

The size, quantity, and shape of the rock fragments 106 can vary. For example, rock fragment 106B can be particle-sized (for example, a grain of sand) that flows with the produced oil 114 through the wellbore 102 to the ground surface 110. Rock fragment 106A can be larger than rock fragment 106B and can be too large to flow through the wellbore 102. The rock fragments 106 can accumulate to form at least one restriction 108 within the reservoir. In some examples, the restriction 108 significantly decreases the production of oil 114 from the reservoir. For example, in some cases, the produced oil 114 can decrease to less than 10% of unobstructed flow when at least one restriction 108 is present in the reservoir.

The systems and methods include a computer system 116 that is operable to perform one or more computer-implemented steps of this disclosure. For example, the computer system 116 determines locations within the formation 104 where rock fragments 106 are likely to form based on whether compressive stresses are less than, equal to, or exceed a compressive strength of the formation 104.

For example, the computer system 116 determines that region 112A has a high probability of rock fragments 106 forming, region 112B has a medium probability of rock fragments 106 forming, and the formation outside region 112B has a low probability of rock fragments 106 forming. In some examples, the computer system 116 defines region 112A as the region of formation 104 where the compressive stress in the formation 104 is greater than the compressive strength of the formation 104. In some examples, the computer system 116 defines region 112B as the region of formation 104 where the compressive stress in the formation 104 is less than but near (for example, within 10% of) the compressive strength of the formation 104.

In some examples, the computer system 116 defines region 112A as the region of formation 104 where the probability of rock fragments 106 forming are above a first threshold (for example, above 90%). In some examples, the computer system 116 defines region 112B as the region of formation 104 where the probability of rock fragments 106 forming are above a second threshold (for example, above 70%) and below the first threshold.

FIG. 2A is a schematic 120 of an in-situ stress state of a formation. In the example shown, the wellbore 102 is initially cylindrical (for example, as a result of being drilled). The overburden and underburden subject the formation 104 surrounding the wellbore 102 to an in-situ stress state having a maximum stress component 122 and a minimum stress component 124. In this example, both the maximum stress component 122 and the minimum stress component 124 are compressive. The compressive stress state can be so severe that the compressive stresses exceed the compressive strength of the formation 104 in regions 126. In some examples, regions 126 are similar to or the same as region 112A shown in FIG. 1. Cavings and rock fragments are likely to form in regions 126.

FIG. 2B is a schematic 130 of a bedding plane anisotropy state of a formation. Anisotropy in the formation 104 means that the formation 104 surrounding the wellbore 104 has two diametrically opposite regions 134 where the bedding planes 132 are tangent to the wellbore 102. Cavings and rock fragments are likely to form in regions 134.

In addition to, and/or instead of, the in-situ stress state shown in FIG. 2A and/or the bedding plane anisotropy state shown in FIG. 2B, the formation of rock fragments 106 can also be influenced by the production history of the wellbore 102. For example, the probability of rock fragments 106 forming is further based on drill bit velocity (for example, the velocity at which the drill descends into the formation 104). In some examples, the probability of rock fragments 106 forming is proportional to drill bit velocity such that faster drilling causes higher probabilities of rock fragments 106 forming in the wellbore 102.

The systems and method also measure physical properties (wellbore diameter, rock density, elasticity, etc.) within one or more wellbores. In some examples, the computer system 116 uses the measured physical properties as input conditions to a finite element model of the wellbore to predict rock fragments and restrictions. In some examples, the computer system 116 uses the measured physical properties to validate the results of the finite element model.

Figure 3A:
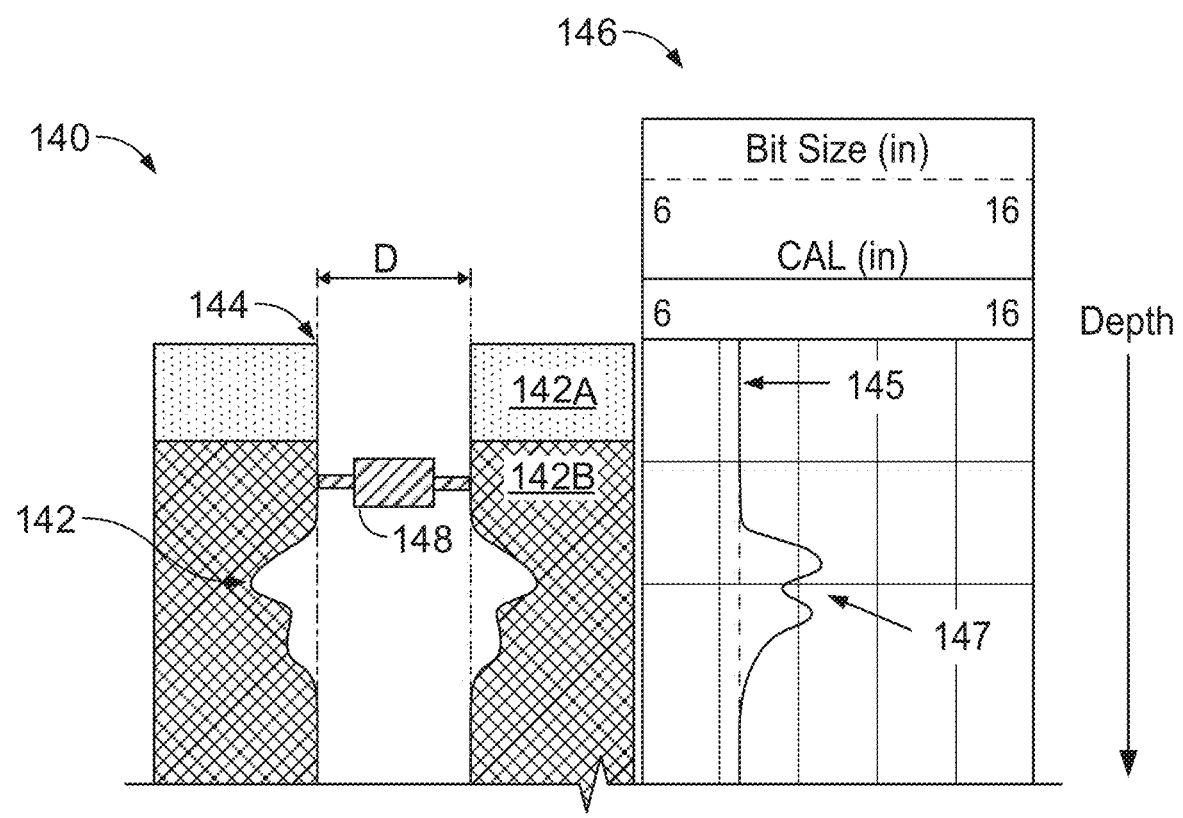
FIG. 3A is a schematic of cavings within a wellbore.

FIG. 3A is a schematic 140 of cavings 142 within a wellbore 144. In some examples, the wellbore 144 is similar to or the same as wellbore 102. Cavings 142 represent a void or depression in a formation (for example, formation layer 142B) after a portion of the formation 142B has failed and has broken-free to form one or more rock fragments (for example, the rock fragments 106 described with reference to FIG. 1). Once the rock fragments 106 have separated from the formation layer 142B, the wellbore 144 is said to be "caved in," and/or have "cavings" present in the formation layer 142B surrounding the wellbore 144.

The systems and methods use a well logging tool 148 (e.g., a caliper log) to measure the diameter of the wellbore 144. For example, an engineer lowers the well logging tool 148 (and/or the computer system 116 controls the well logging tool 148 to be lowered) into the wellbore 144 to measure the diameter 146 of the wellbore 144 as a function of depth in the wellbore 144.

Figure 3B:
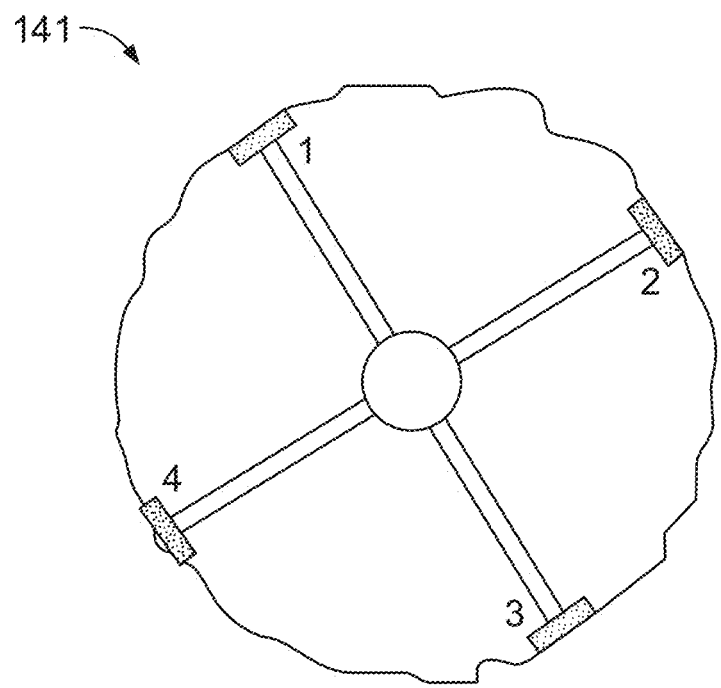
FIG. 3B is a schematic of four radial measurements of a wellbore.

FIG. 3B is a schematic 141 of four radial measurements of a wellbore. In the example shown, the caliper wireline log data from the well logging tool 148 contains several radial measurements at each measured depth point. The depth point with the smallest radial measurement is designated as smallest flow channel. Example results of the wireline log caliper measurements are shown in Table 1 below.

TABLE 1

Visual illustration of radial measurements 1, 2, 3, 4 at a single measured depth point.

| Measured Depth, ft | Radial Measurement 1 (inch) | Radial Measurement 2 (inch) | Radial Measurement 3 (inch) | Radial Measurement 4 (inch) |
|---|---|---|---|---|
| 13,000.0 | 2.9375 | 3.1545 | 3.0156 | 2.8756 |
| 13,000.5 | 3.2156 | 3.0124 | 2.7856 | 3.3152 |

As the well logging tool 148 passes through the first layer of formation 142A (which can be similar to or the same as formation layer 104A), the well logging tool 148 measures the diameter 146 (e.g., by physically contacting the sidewall of the wellbore or by non-contact means (for example, lasers)). In this example, cavings are not present in formation 142A so the measured diameter is approximately equal to the drill bit diameter D that was used to drill the wellbore 144 (represented by location 145). As the well logging tool 148 passes through formation layer 142B, the well logging tool 148 measures a varying diameter as a function of depth within the wellbore 102 (represented by location 147). The systems and method determine that a caving is present based on a deviation of the measured diameter from the drill bit diameter D as a function of depth in the wellbore 144.

The probability of forming a restriction 108 is exacerbated by the following drilling-related scenarios. There is a higher risk of forming a restriction 108 when enlargements, breakouts, washouts, and wellbore failure occurred during the drilling of the wellbore 102. For example, already enlarged sections 112 have a higher tendency for further enlargement compared to wellbores 102 without such enlarged sections 112. Also, the rock fragments produced from the already enlarged sections can accumulate in the non-enlarged sections to create bottlenecks. Such bottlenecks lead to a higher probability of path blockage.

There is also a higher risk of forming a restriction 108 when the reservoir interval is subjected to elevated and cyclical loads during the drilling of the wellbore 102. The elevated and cyclical loads can result from elevated mud weight values, drill-string surge events, well control operations and well stimulation operations. Elevated and cyclic loads can lead to the creation of yield zones around the wellbore. The yield zones have a high likelihood of completely failing compared to wellbores that have not been exposed to elevated and cyclic loads.

Figure 4:
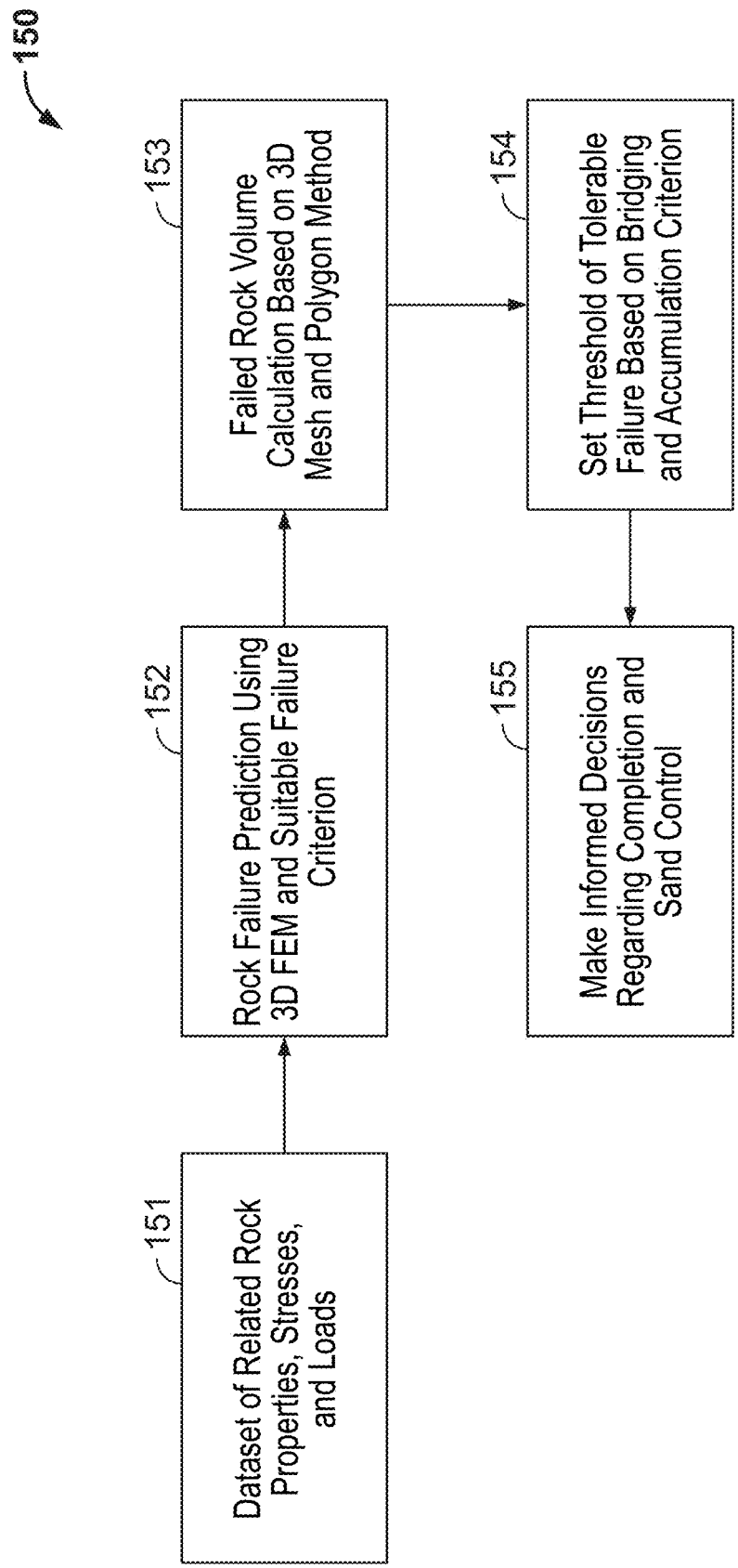
FIG. 4 is a flow chart of a method for selection and installation of a wellbore completion setup.

FIG. 4 is a flow chart 150 of a method for selection and installation of a wellbore completion setup. At block 151, a computer system (for example, the computer system 116) determines and/or receives a dataset of rock properties, stresses, and loads of the wellbore 102 and formation 104. For example, the rock properties include compressive strength, one or more parameters of a failure criterion, properties of at least one plasticity model, an elastic modulus, and/or a density of each formation layer 104A, 104B of the formation 104. In some examples, the computer system 116 extracts a core sample from the formation 104, determines, by testing the extracted core sample, the compressive strength of the formation 104, and determines one or more parameters of a failure criterion (for example, a Mohr-Coulomb failure criterion, a Mogi failure criterion, or a modified Drucker-Prager failure criterion) based on the determined compressive strength of the formation 104. In some examples, the computer system 116 determines and/or receives the stresses (for example, the in-situ stresses) and/or loads (for example, pore-pressures within the wellbore 102, fluid pressures, etc.) based on a regional model of the formation 104, from one or more logs of the wellbore 102, and/or from one or more logs from neighboring wellbores.

At block 152, the computer system 116 predicts rock failure using a three-dimensional finite element model in combination with a failure criterion. Details regarding the finite element model are described with reference to FIGS. 5A, 5B, 6, and 7. In some examples, one or more of the rock properties, stresses, and loads of the wellbore 102 and formation 104 are used as input conditions in the finite element model to predict rock failure (e.g., predict when a region of the formation 104 is likely to fail). This prediction is based on whether the compressive stresses of the nodes of the finite element model exceed a failure criterion.

At block 153, the computer system 116 determines the volume of failed rock based on a post-processing of the results of the finite element model. Details regarding the post-processing of the finite element model to determine a volume and a size of the rock fragments 106 are described with reference to FIGS. 8A and 8B. In some examples, the computer system 116 determines (and/or an engineer determines) a polygon that encapsulates the nodes that have failed using the results of the finite element model and the size. The volume of the polygon represents the size and volume of the rock fragments 106.

At block 154, the computer system 116 determines a probability that a restriction 108 will form in the reservoir based on a bridging and accumulation criterion. Details regarding determining the probability that a restriction 108 will form are described with reference to FIGS. 9, 10, 11, 12A, 12B, 13, 14A-C, and 15A-C. In some examples, the probability is determined based on the flow rate of the oil 114 within the reservoir and the size and/or volume of the rock fragments 106.

At block 155, the computer system 116 selects a wellbore completion setup. In some examples, the computer system 116 controls an installation process to install (and/or an engineer installs) the selected completion setup in the wellbore 102. For example, computer system 116 selects the completion setup to be an open-hole completion when the probability is less than a first threshold (for example, less than 50%). In some examples, the systems and methods select the completion setup to be an open-hole with a gravel pack completion setup when the probability is between the first threshold and a second threshold (for example, less than 75%). In these cases, the first threshold is less than the second threshold. In some examples, the systems and methods select the completion setup to be a cased and perforated completion setup when the probability is greater the second threshold.

In some examples, the computer system 116 controls (and/or an engineer adjusts) one or more conditions within the wellbore 102 to lower the probability that a restriction 108 will form instead of, or in addition to, installing a wellbore completion setup. For example, the computer system 116 adjusts a pump to increase the flow rate of the oil 114 to lower the probability that a restriction 108 will form.

Figure 5A:
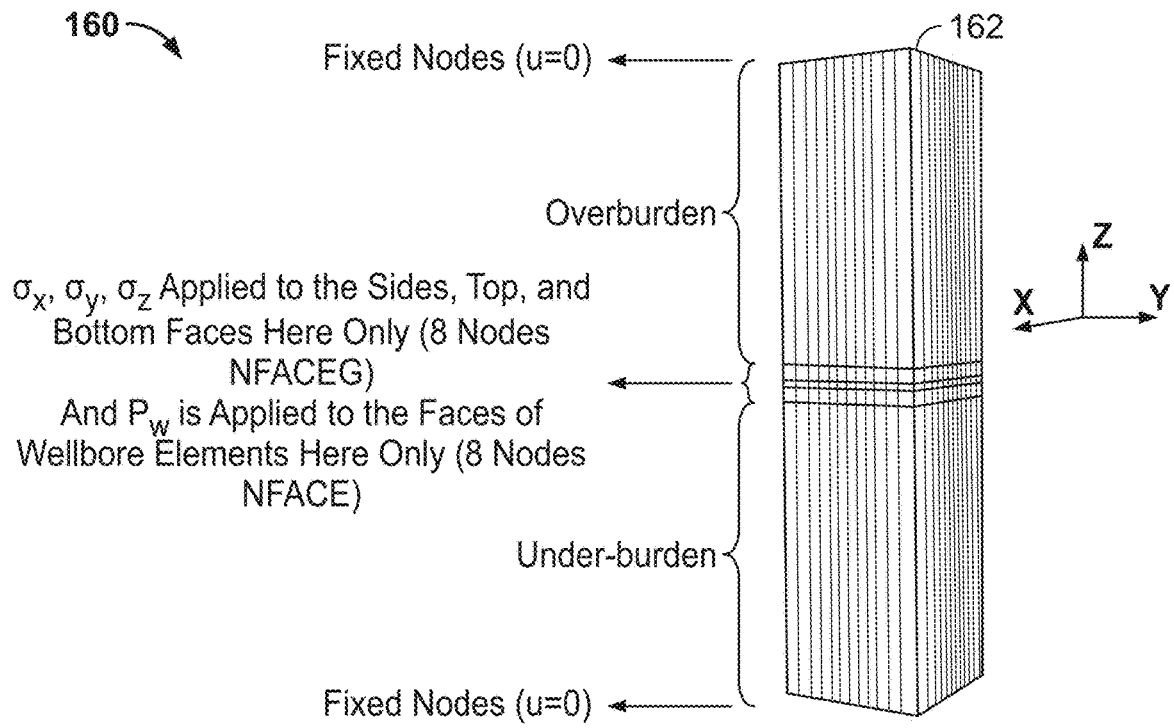
FIGS. 5A and 5B are illustrations of a three-dimensional finite element model for determining stresses in a formation surrounding a wellbore.
Figure 5B:
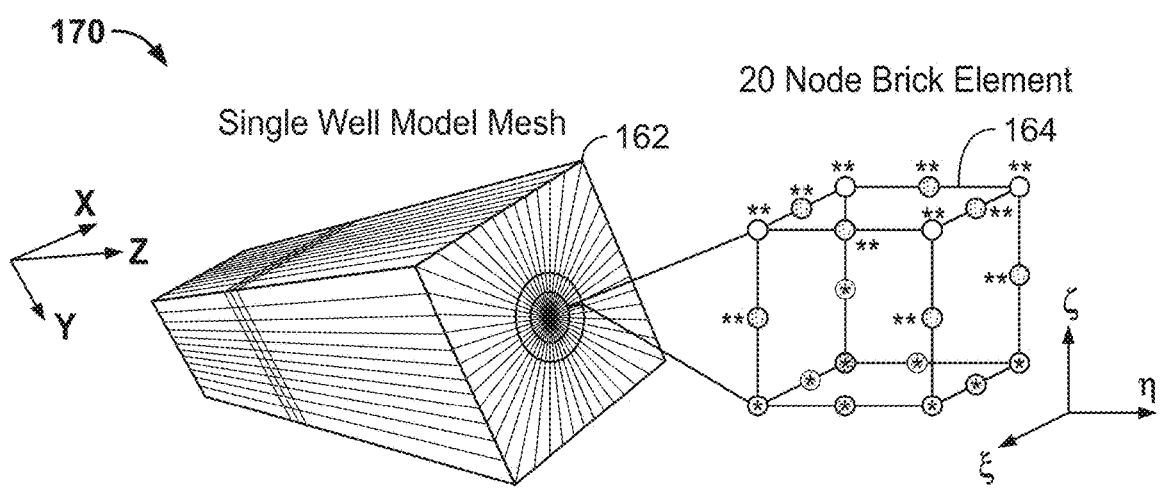

FIGS. 5A and 5B are illustrations 160, 170 of a three-dimensional finite element model 162 for determining stresses in a formation surrounding a wellbore. In some examples, the finite element model 162 represents a three-dimensional finite element model of the wellbore 102 and the formation 104 surrounding the wellbore 102. In some examples, the finite element model 162 is a geomechanics model having an elasto-plastic solution capability. For example, the finite element model 162 solves for elastic and plastic material behavior of rocks of the formation). The finite element model 162 includes finite elements 164 that include 20-node (quadratic) brick elements. The finite element model 162 includes a physical model of overburden, under-burden, and the wellbore. The computer system 116 creates the finite element model 162, assigns loads, and assigns heterogeneous material properties to the finite elements 164 as part of a pre-processing phase.

The computer system 116 solves the finite element model 162 to determine the cumulative influence of drilling mud weight variations, cyclic loads, drilling-induced wellbore enlargements, and production or depletion history to predict rock yielding and failure. The output of the finite element model 162 is used to predict a volume of rock fragments surrounding the wellbore 172. The output of the finite element model 162 is integrated with an accumulation or bridging criteria that defines the limits and conditions at which production is predicted to be blocked based on the volume of rock fragments.

The computer system 116 solves the finite element model 162 by minimizing the total potential energy of the finite element model 162, which produces the following equilibrium condition:

$$u\int_{V^e}((B^T)DB)d\Omega = \int_{V^e} N^T F d\Omega - \int_{S^e} N^T T d\Gamma \quad (1)$$

where u is the displacement, B and $B^T$ are the strain-displacement matrix and its transpose, respectively. $N^T$ is the transpose of the quadratic Serendipity shape functions vector, which are derived for the 20-nodes isoparametric brick elements 164 shown in FIG. 5B, D is the consistent tangent matrix, which is formulated based on the mechanical properties of the rock, F is the body force, and T is the traction force. The body and traction forces represent the in-situ stresses and mud weight loading on the wellbore. The integrations in equation (1) are performed over an element volume ($V^e$) with respect to the volume variable ($\Omega$) or over an element surface ($S^e$) with respect to the area variable ($\Gamma$). The matrix resulting from the integral in the expression to the left is known as the stiffness matrix ($K^e$).

The finite element model 162 uses a plastic flow rule for strain hardening to predict the plastic behavior of the rock, which occurs when the stresses are greater than the yield point. This means that the total strain is the addition of two components, which are poro-elastic strain ($\varepsilon^e$) and a plastic strain ($\varepsilon^p$). The plastic flow rule assumes that the flow direction is perpendicular to the yield surface $\psi$ and it is defined as:

$$\Delta\varepsilon_{ij}^p = \lambda \frac{\partial \psi(\sigma_{ij})}{\partial \sigma_{ij}} \quad (2)$$

where $\varepsilon_{ij}^p$ is the plastic strain tensor, $\sigma_{ij}$ is the stress tensor, and $\lambda$ is the plastic strain multiplier.

The associative flow rule is applied by assuming that the plastic potential surface is the same as the yield surface $\psi$. It also assumes the yield surface expands without changing the flow direction. The yield criterion is the Drucker-Prager criterion, where yielding will take place when the deviatoric stress tensor ($S_{ij}$) and the mean stress ($\sigma_m$) satisfies the following relationship:

$$\psi(\sigma_{ij}) = \sqrt{\frac{1}{2}S_{ij}S_{ij}} - a_0 + a_1\sigma_m = 0 \quad (3)$$

where constants $a_0$ and $a_1$ are determined experimentally as material properties and are used to correlate the Drucker-Prager criterion to the Mohr-Coulomb criterion.

The following expression for strain hardening is then used to calculate the scalar plastic strain $\varepsilon^p$ from the plastic strain tensor determined by the flow rule:

$$\varepsilon^p = \int \sqrt{\frac{2}{3}d\varepsilon_{ij}^p d\varepsilon_{ij}^p} \quad (4)$$

Figure 6:
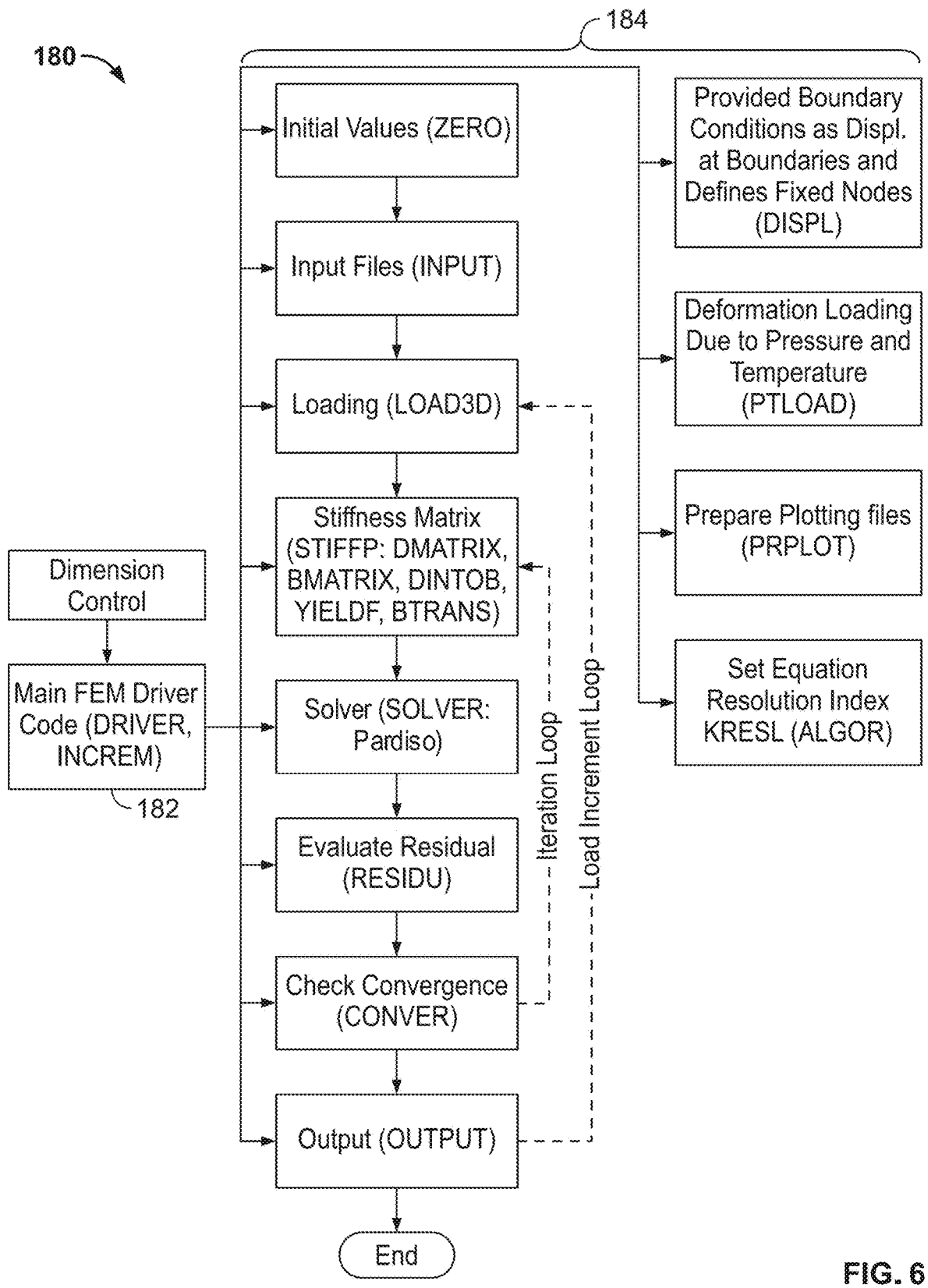
FIG. 6 is a flow chart of a driver computer code of the finite element model that includes the main subroutine and twelve subroutines.

FIG. 6 is flow chart 180 the solution process executed by the computer system 116 to solve the finite element model 162. The finite element model 162 is solved using thirty-three subroutines and a driver code 182, some of which are shown in FIG. 6. The driver code 182 calls twelve main subroutines 184 and these perform several functions including receiving the input file, applying loads to construct and assemble the global stiffness matrix, and solving the system of equations.

Upon solving the system of equations, as described by Equation (1), and determining the displacements u, the residual forces are calculated to check for convergence and equilibrium by subtracting the left-hand side from the right-hand side in the global form, where the left-hand side is the global stiffness matrix multiplied by displacement and the right-hand side is the body and traction forces. The value obtained from the subtraction of these two quantities should be equal to zero if the equilibrium condition is fully satisfied. However, that is not always achievable, therefore, a tolerance value is set to check for convergence. The tolerance value is usually set to be close but not equal to zero.

Once the residual forces are calculated and found to be less than the set tolerance value, convergence is said to be achieved, otherwise, the residual forces are carried to the next iteration. The same process is repeated for each separate load increment, where the load increments are defined in the input file manually. These processes are carried out in two loops with the convergence loop (or "iteration loop") nested in the load increment loop as shown in FIG. 6. The computer system 116 post-processes the finite element model 162 after convergence is achieved.

The computer system 116 uses one or more failure criterion models of rock and soil failure to determine rock fragments 106. For example, a Mohr-Coulomb criterion, a Mogi criterion, a Drucker-Prager criterion, and a Lade criterion can be used to determine rock fragments 106. In some examples, the models rely on lab testing to define the failure envelope of rocks. A failure envelope is defined by strength parameters which are specific to each developed model and are limited to certain limits of shear and normal stresses as observed in lab testing. These models suggest that rock failure in compression will take place if the stress state of the rock at the specific strength parameters is above the defined failure envelope.

Figure 7:
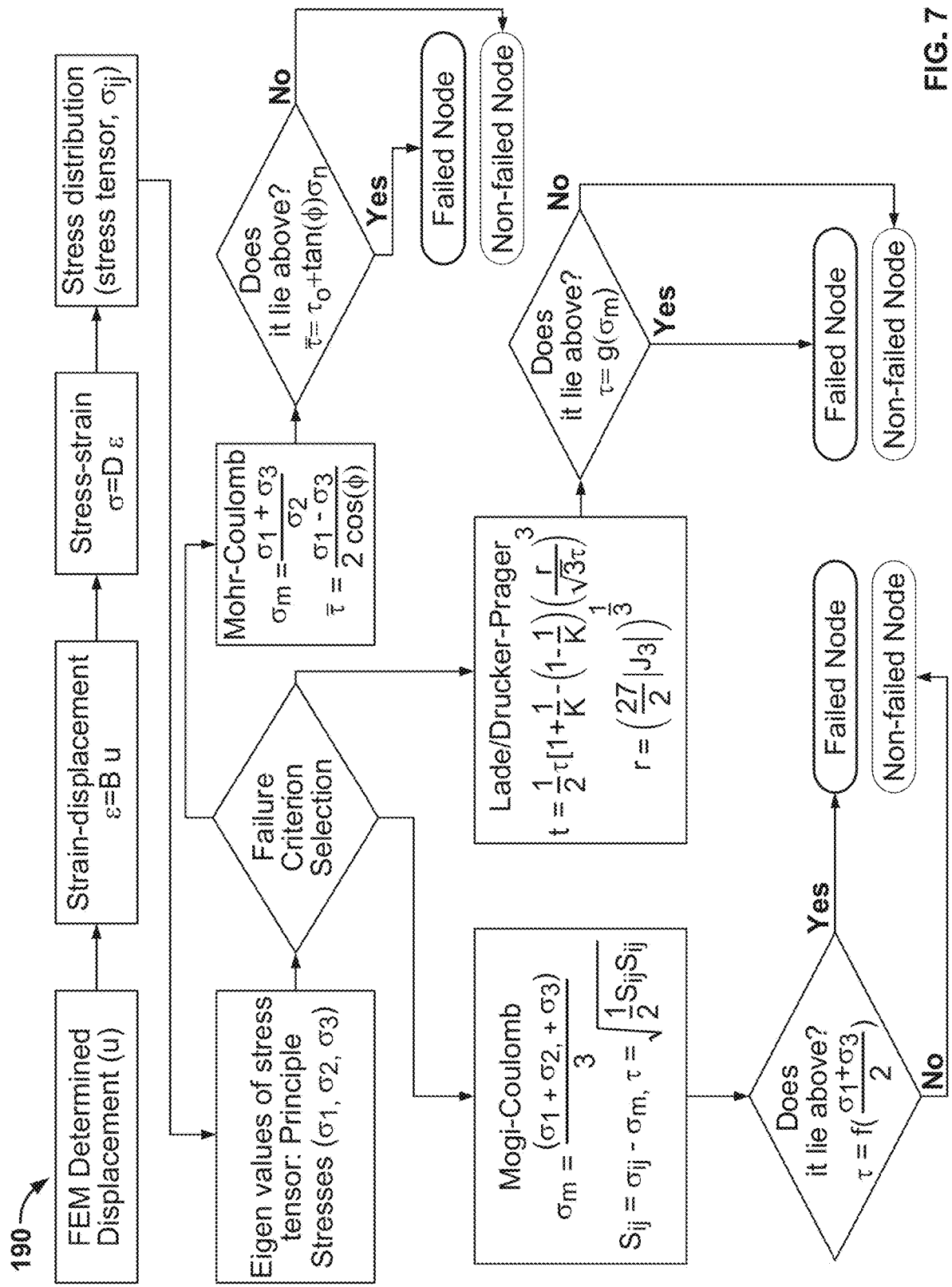
FIG. 7 is a flow chart of a method to determine whether nodes of an element of the finite element model have failed based on one or more failure criterions.

FIG. 7 is a flow chart 190 of a method to determine whether nodes of an element of the finite element model have failed as part of a post-processing phase. The role of the failure criteria is to evaluate the stress state at each point (for example, at each integration point for each finite element 164 of the finite element model 162) against the strength parameters assigned to that particular integration point to determine whether that integration point has failed.

For example, if the computer system 116 uses the Mogi failure criterion, the principle stresses calculated from the finite element model ($\sigma_1$, $\sigma_2$, $\sigma_3$) is used to determine the value of the octahedral shear stress ($\tau$). Next, the failure criterion function (f) is calculated based on the strength parameters values assigned to each point. Finally, the value obtained from the failure criterion function (f) is subtracted from the calculated value of the octahedral shear stress ($\tau$). If the computer system 116 determines that the result of this subtraction is a positive value (meaning that this point lies above the failure envelope), the computer system 116 determines that this point is predicted to fail.

An illustration of this process and the related expression for each conventional failure criterion are shown in FIG. 7. In some implementations, the computer system 116 evaluates failure using multiple failure criteria to assess a best fitting one for each rock type. In all of the expressions in FIG. 7, the convention for compressive stress is negative.

Once the computer system 116 solves the finite element model 162 and determines integration points that have failed, the computer system 116 extrapolates the stresses and failure to the nodes of the finite elements. The computer system 116 post-processes each finite element to determine the volume of the failed elements. This volume is used to determine the size of the rock fragments. In some implementations, the computer system 116 uses shear failure zones mapping, cavings extensions, and enlargements beyond the wellbore uniform diameter to determine the failed rock volume.

Figure 8A:
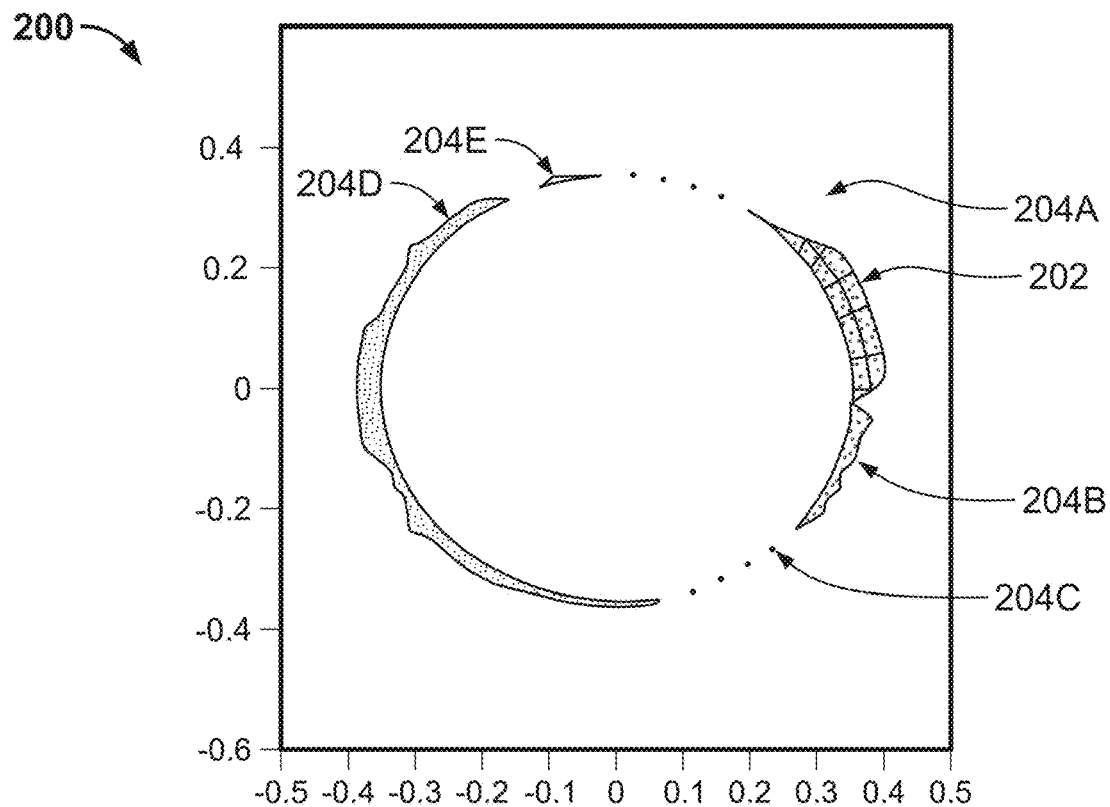
FIGS. 8A and 8B are plots of regions of formation that exceed threshold stress defining formation fragments that can break free from the formation.
Figure 8B:
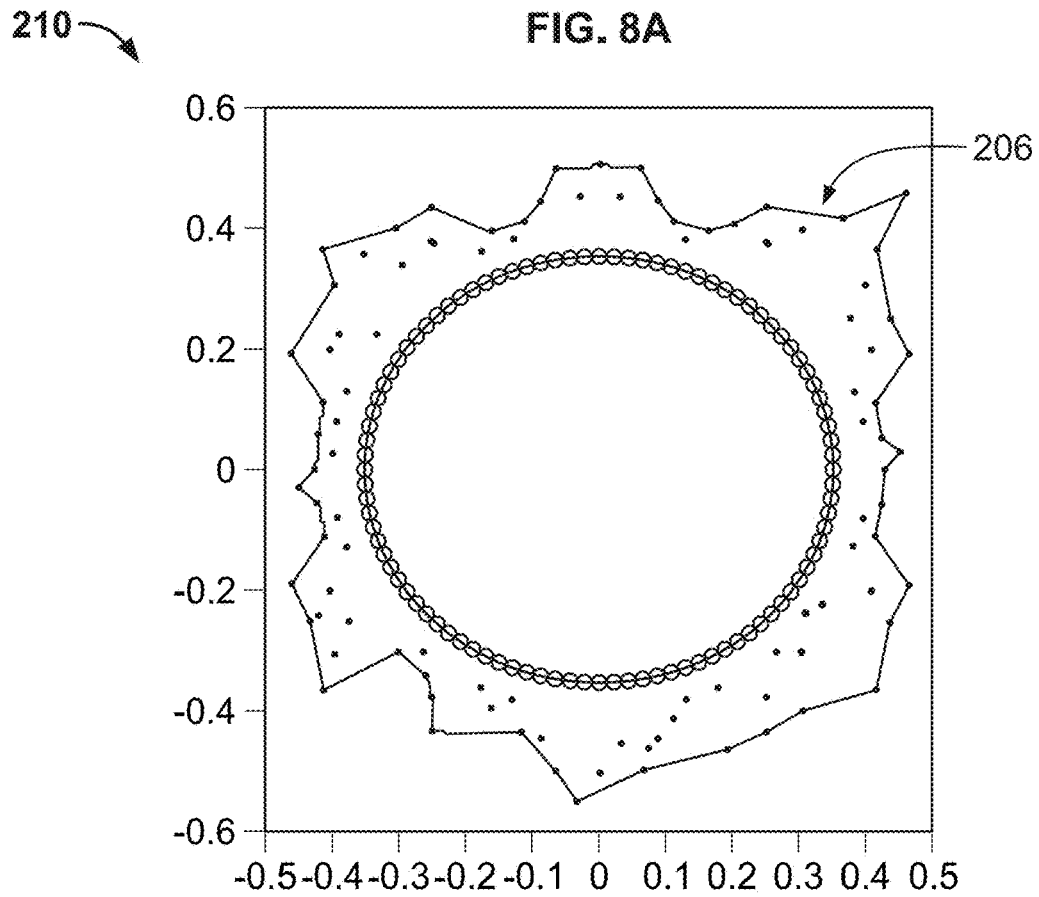

FIG. 8A is a plot 200 of disconnected regions surrounding a wellbore where cavings are predicted to develop and FIG. 8B is a plot 210 of a single region surrounding a wellbore where cavings are predicted to develop. While the plots 200, 210 are two-dimensional, the predicted stress field is three-dimensional and can represent non-uniform failure patterns.

In some implementations, the computer system determines the volume for each caving using one or more polygons. Using the polygon approach, the failed mesh nodes as predicted by the finite element model 162 are extracted. Next, the volume enclosed by the extracted nodes in a three-dimensional space is calculated as the predicted failed rock volume. Since the distribution of failure zones predicted by the finite element model 162 can be non-uniform and irregular, simplified symmetry rules are not always applicable when calculating the area enclosed by failed nodes at each vertical layer along the borehole axis. Therefore, the computer system 116 retrieves the coordinates of the failed mesh nodes and determines a polygon around each discrete failure region in each layer of mesh nodes. In some implementations, the computer system 116 executes a convex hull algorithm to determine the boundary of each discrete failure region.

The area of each polygon is estimated by dividing the entire region into discrete uniform geometric shapes. The definition of each polygon is based on the failed mesh nodes information and on the size of the mesh. For example, if a group of failed nodes are surrounded by non-failed nodes, the failed nodes will be considered as separate regions 204A-204E as shown in FIG. 8A, and hence, a separate caving fragment. On the other hand, if the failed zones are all interconnected to each other around the wellbore with no non-failed nodes intersecting them, a single polygon 206 is defined around the wellbore to determine the failed region area as shown in FIG. 8B.

For example, the computer system 116 determines that the wellbore has twelve disconnected regions 204A-204E where cavings are predicted to develop at this cross-section of the wellbore. The formation within these regions 204A-204E are predicted to break-free and form at least twelve rock fragments. For example, region 204C represents small rock fragments (for example, particulate-sized fragments), regions 204A, 204B, and 204E represent medium-sized rock fragments, and region 204D represents a large rock fragment.

Once the volumes of time-dependent rock failure are predicted, the volumes are incorporated into a particle settlement, bed accumulation, and bridging criteria to predict the location within the wellbore where a restriction in the flow path to the reservoir will develop. In some implementations, the criteria depends on (a) the size of failed rock fragments predicted to separate (or spall) from the formation at each time interval (for example, as determines using the polygons as described with reference to FIGS. 8A and 8B), (b) the wellbore fluid flow rate, transportation velocity, and spalled rock fragments settling velocity as described below, and (c) the actual size or diameter variations throughout the wellbore (for example, as measured using tool 148 as described with reference to FIGS. 3A and 3B).

Figure 9:
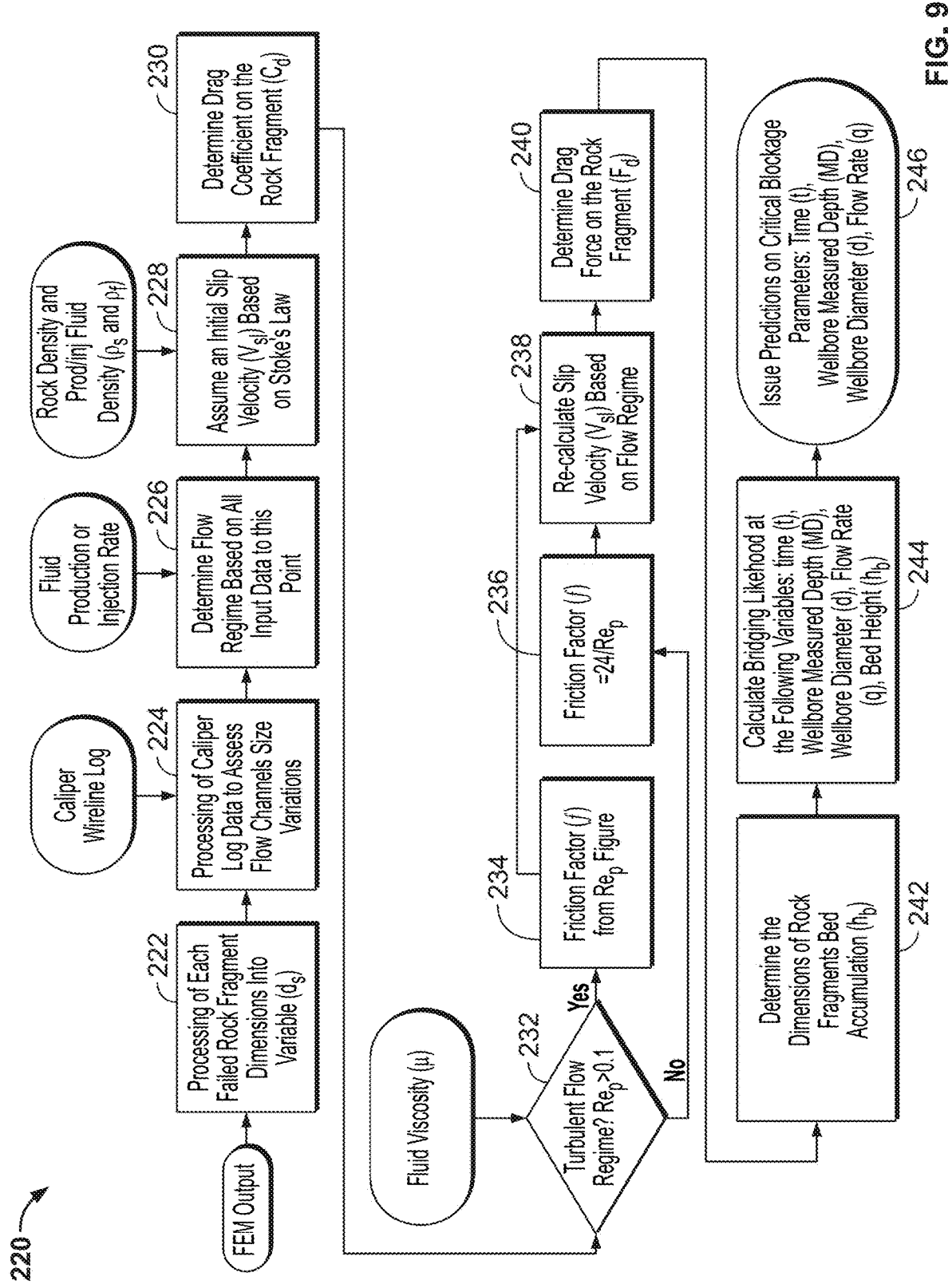
FIG. 9 is a flow chart of a method for selection and installation of a wellbore completion setup emphasizing aspects related to the fluid of the wellbore.

FIG. 9 is a flow chart 220 of a method for predicting a probability of at least one restriction forming in the reservoir. At block 222, the computer system 116 determines an effective diameter ($d_s$) for each failed rock fragment as predicted from the finite element model based on the volume determination. For example, the computer system 116 determines the failed rock fragments dimensions (for example, volume, width, length, height, diameter), based on the results from the finite element model 162. The dimensions of the failed rock fragments vary over time. The collection of all failed rock fragments dimensions (for example, over space and time) define a particle size distribution (PSD).

The computer system 116 determines an effective diameter ($d_s$) to these rock fragments since the failed rock fragments are not always spherical (for example, the rock fragments shown in FIGS. 8A and 8B are not spherical). In some implementations, if the rock fragment is a rectangular prism, the computer system 116 determines the effective diameter ($d_s$) as the maximum value among the rock fragment's height, width, and length which are measured in a similar manner as the volume calculation described with respect to FIGS. 8A and 8B. In some implementations, if the rock fragment is spherical, the computer system determines the effective diameter ($d_s$) as a diameter which is measured in a similar manner as the volume calculation described with respect to FIGS. 8A and 8B.

At block 224, the computer system 116 receives caliper wireline log data and processes the caliper wireline log data to determine flow channel size variations in the wellbore. For example, the well logging tool 148 described with reference to FIG. 3A measures the diameter of the wellbore as a function of depth in the wellbore. The well logging tool 148 generates the caliper wireline log data which represents the wellbore diameter as a function of depth in the wellbore. The computer system 116 receives the caliper wireline log data from the well logging tool 148 and/or from a computer storage medium storing the caliper wireline log data and processes the caliper wireline log data to determine flow channel size variations in the wellbore. In some examples, the computer system 116 determines the minimum channel size and location based on the caliper wireline log data using minimum and maximum value determination functions as described with reference to FIG. 3B.

At block 226, the computer system 116 receives fluid production or injection rate data and determines a flow regime based on the determined flow channel size variations in the wellbore from block 224 and the determined effective diameter ($d_s$) from block 222. The fluid production rate data represents the flow rate (for example, in units of volume/time) of the fluid being extracted from the reservoir.

In the context of the example described with reference to FIG. 1, the production fluid is the oil 114 and the fluid production rate represents the volumetric flow rate of oil 114 being extracted from the reservoir through the wellbore 102 (for example, through a pump or a waterflooding operation). The remaining blocks of flow chart 220 detail how the computer system 116 determines a probability of at least one restriction developing based on either the production fluid or an injection fluid (for example, from a water flooding operation).

In some implementations, the computer system 116 determines the flow regime by determining the Reynolds number of the flow. In some implementations, the computer system 116 determines the Reynolds number of the flow using the following expression:

$$Re_p \text{(Particle Reynold's number)} = \frac{V_{sl} d_s \rho_f}{\mu} \quad (5)$$

where $V_{sl}$ is the initial slip velocity defined in block 228, $\rho_f$ is the production/injection fluid density, and $\mu$ is the production/injection fluid viscosity.

At block 228, the computer system 116 receives rock density ($\rho_s$) and production/injection fluid density ($\rho_f$) and determines an initial slip velocity ($V_{sl}$) based on Stoke's law using the rock density ($\rho_s$) and the production/injection fluid density ($\rho_f$). As noted in block 226, the determined initial slip velocity ($V_{sl}$) is then used to determine the flow regime. In some implementations, the computer system 116 determines the initial slip velocity ($V_{sl}$) using the following expression:

$$V_{sl}\text{(Stoke's law slip velocity, m/s)} = \frac{d_s^2 g(\rho_s - \rho_f)}{18\mu} \quad (6)$$

where g is the gravitational constant (g=9.81 m/s$^2$).

At block 230, the computer system 116 determines a drag coefficient ($C_d$) of the rock fragment. In some implementations, the computer system 166 determines the drag coefficient ($C_d$) based on the following equation:

$$C_D\text{(Drag Coefficient)} = \frac{4}{3} \frac{g d_s (\rho_s - \rho_f)}{V_{sl}^2 \rho_f} \quad (7)$$

where each of these parameters have been previously defined.

At block 232, the computer system 116 receives fluid viscosity ($\mu$) data and determines whether the determined flow regime has a Reynolds number greater than 0.1. In equation form, this condition reads:

$$Re_p > 0.1 \quad (8)$$

where each of these parameters have been previously defined. If equation (8) is true, then the flow regime is considered "turbulent." If equation (8) is false, then the flow regime is considered "laminar."

If the computer system 116 determines that the flow regime is turbulent, the computer system 116 proceeds to block 234 to determine a Darcy fraction factor (f). In some examples, the friction factor (f) represents the head loss, or pressure loss, due to friction along a given length of the wellbore to the average velocity of the fluid flow of the production/injection fluid in the wellbore. The computer system 116 uses the friction factor to determine the particle slip velocity as described in detail below.

In some implementations, the computer system 116 determines the friction factor (f) using a look-up table or chart such as a Moody diagram. In some examples, the computer system 116 uses the Moody diagram shown in FIG. 10 to determine the friction factor (f) based on the Reynolds number ($Re_p$) and the drag coefficient ($C_d$).

Figure 10:
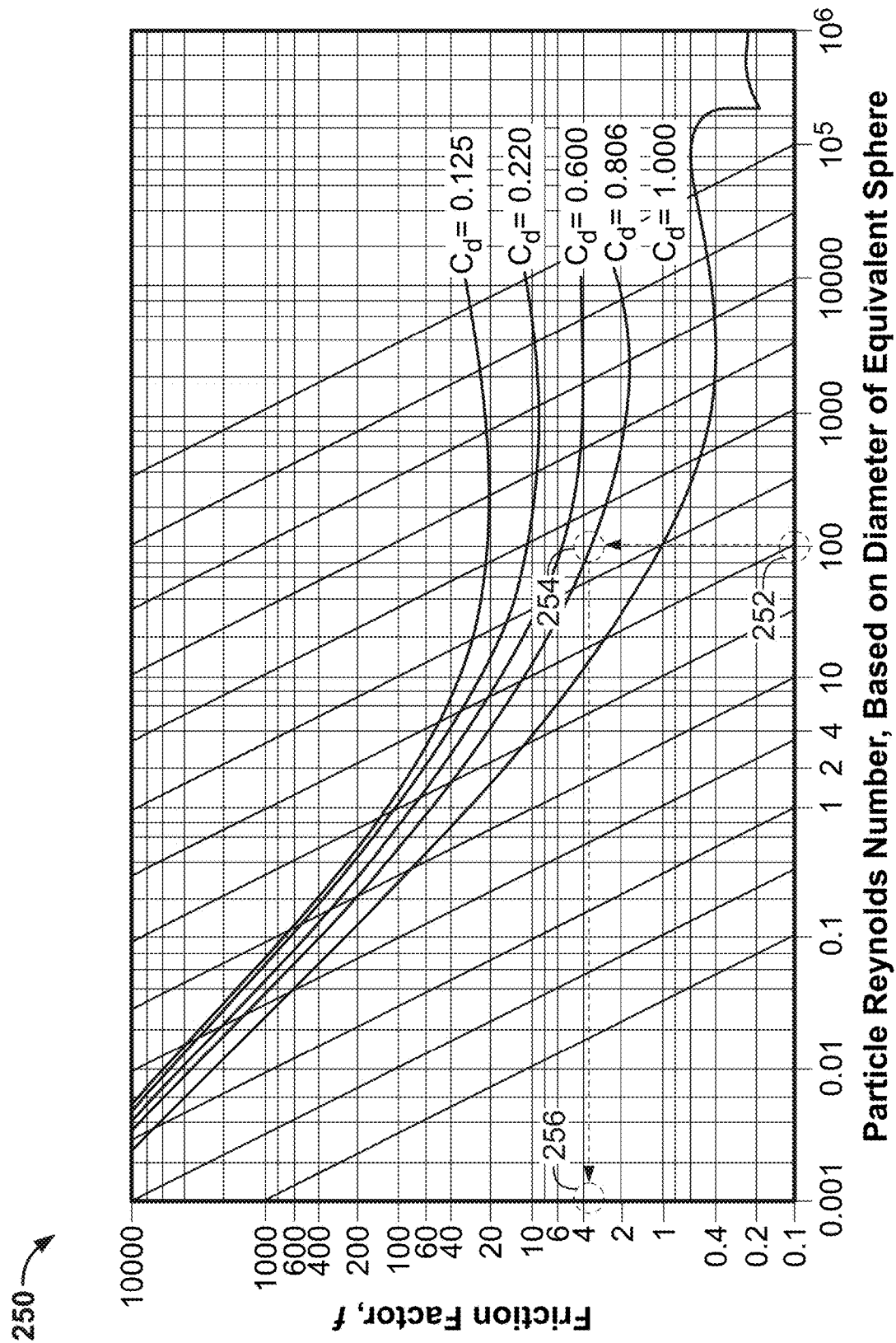
FIG. 10 is a Moody diagram for determining the friction factor for turbulent flow based on drag coefficient and Reynold's number.

FIG. 10 is a Moody diagram 250 for determining the friction factor (f) for turbulent flow based on drag coefficient ($C_D$) and Reynold's number ($Re_p$). The computer system 116 maintains a digital representation of this FIG. 10 and can perform the following look-up process. Starting with a Reynolds number, for example, Re=100 as shown in bubble 252, a vertical line (Re=constant) is traversed until the vertical line intersects a curve associated with the determined drag coefficient ($C_d$), for example, at bubble 254 representing $C_d$=0.806. A horizontal line (f=constant) is then traversed until the horizontal line intersects the vertical axis, for example, at bubble 256 indicating the friction factor (f) to be between 2 and 4 (for example, f=3.5).

Referring to FIG. 9, if the computer system 116 determines that the flow regime is laminar, then the computer system 116 proceeds to block 236 to determine the fraction factor (f). In some implementations, the computer system 116 determines the friction factor (f) using the following expression when the determined flow regime is laminar:

$$f \text{ (friction factor)}|_{Re_p \leq 0.1} = \frac{24}{Re_p} \quad (9)$$

With the friction factor (f) computed based on whether the determined flow regime is laminar or turbulent, the computer system 116 proceeds to block 238 to re-calculate the particle slip velocity ($V_{sl}$) based on the friction factor (f) if necessary. In some implementations, the computer system 116 maintains the definition of the particle slip velocity ($V_{sl}$)

based on equation (6) if the determined flow regime is laminar and updates the slip velocity ($V_{sl}$) using the following expression if the determined flow regime is turbulent:

$$V_{sl}(\text{Turbulent flow slip velocity, m/s}) = \frac{2}{3}\sqrt{\frac{3gd_s(\rho_s - \rho_f)}{f \cdot \rho_f}} \quad (10)$$

where each of these parameters have been previously defined.

At block 240, the computer system 116 determines the drag force on the rock fragment ($F_d$). In some implementations, the computer system 116 determines the drag force ($F_d$) using the following expression:

$$F_d(\text{Total drag force},N) = 3\pi\mu d_s V_{sl} \quad (11)$$

where each of these parameters have been previously defined and the particle slip velocity ($V_{sl}$) is based on whether the flow regime is laminar or tubular as described with reference to block 238.

At block 242, the computer system 116 determines the dimensions of the rock fragments bed accumulation. In some implementations, the dimensions include a bed accumulation height ($h_b$). In some implementations, the computer system 116 determines the dimensions of the rock fragments bed accumulation based on the failed rock fragments dimensions and the settling velocity which is equal to the slip velocity ($V_{sl}$). In some implementations, the computer system 116 determines the bed accumulation height ($h_b$) using the following expression:

$$h_b = \sum_{i=0}^{n}(d_s)_i \quad (12)$$

where n is the total number of rock fragments that settle down in a direction that is perpendicular to the wellbore axis.

At block 244, the computer system 116 determines the probability that at least one restriction will develop in the wellbore. In some examples, the probability that at least one restriction will develop in the wellbore is considered a "bridging likelihood." In some implementations, the computer system 116 determines the probability based on time (t), wellbore measured depth (MD), wellbore diameter (d), flow rate (q), and bed accumulation height ($h_b$).

For example, the computer system 116 uses the volumes of the time-dependent rock fragments from block 222 in a bridging criteria to predict a location within the wellbore where the flow path to the reservoir will be restricted. In some examples, the bridging criteria is based on the following factors: (a) the size of failed rock fragments predicted to spall at each time interval of one or more time intervals (for example, hours, days, weeks, years, etc.); (b) the wellbore fluid flow rate, transportation velocity, and spalled rock fragments settling velocity; and (c) the actual size or diameter variations throughout the wellbore (for example, as measured by the well logging tool 148).

The computer system 116 determines the probability that at least one restriction will develop based on the bridging criteria. For example, the computer system 116 solves the finite element model 162 and uses the results of the finite element model 162 to predict the varying sizes and dimensions of rock fragments that will fail and spall off into the wellbore over time. The computer system 116 uses a bridging criterion based on this information (failed fragments sizes (factor (a) as described in the preceding paragraph) along with the wellbore size (factor (c) as described in the preceding paragraph)) to determine one or more conditions at which the wellbore will be restricted or blocked.

In some implementations, the computer system 116 determines bridging criteria using one or more of the following criteria: the one-third rule, the Vickers criterion, and the Aramco criterion. For example, the one-third rule is based on the following condition:

$$D50 \geq \tfrac{1}{3} \text{ largest effective wellbore diameter} \quad (13)$$

where the D-values refer to the particle size distribution (PSD) of the effective diameter ($d_s$) of failed and spalling rock fragments that were predicted using the finite element model 162.

For example, the computer system 116 determines the probability that at least one restriction will occur using the one-third rule by evaluating whether the D50 value (for example, the mean) of the failed rock fragments is larger than or equal to the wellbore diameter. If this condition is true, then effective bridging is expected to occur as long as the wellbore fluid flow rate is low enough for the failed rock to settle down (which relates to factor (b) as described in the preceding paragraphs). If this condition were false, then effective bridging is not expected to occur.

Regarding the wellbore fluid flow rate being "low enough" for the failed rock to settle down, the computer system 116 receives the fluid flow rate (q), which is often expressed in gallons per minute (gpm), barrels per day (bbl/d), or standard cubic feet per day (scf/d). The computer system 116 converts the fluid flow rate (q) into a velocity value using the wellbore cross-sectional area (A). In some examples, the computer system 116 performs this conversion by evaluating the following expression: v=q/A. This velocity value (v) is used to solve for the q value that is low enough for its corresponding velocity (v) to equal to the slip velocity ($v_{sl}$) calculated by Equations (5)-(12). In this way, the wellbore fluid flow rate being "low enough" for the failed rock to settle down means that the wellbore fluid flow rate (q) is associated with a fluid velocity within the cross-sectional area of wellbore that is equal to or less than the slip velocity ($v_{sl}$) defined by Equation (6).

The bridging criteria relies on the results from Equations (5)-(12) as follows: for the input flow rate (q) and its corresponding velocity, Equations (5)-(12) are used to determine the range of effective diameters ($d_s$) of rock fragments that will settle down. This range will constitute the particle size distribution of deposited or settled down rock fragments. The D-values from this PSD are then used into the applicable bridging criterion.

In some implementations, the computer system 116 uses other bridging criteria to determines the probability that at least one restriction will occur. In some cases, one or more of these bridging criteria are used together.

In some implementations, the computer system 116 determines the probability that at least one restriction will occur using the Vickers criterion by evaluating the following expressions:

$$D90 = \text{largest effective wellbore diameter} \quad (14)$$

$$D75 \leq \tfrac{2}{3} \text{ largest effective wellbore diameter} \quad (15)$$

$$D50 = \tfrac{1}{3} \text{ largest effective wellbore diameter} \quad (16)$$

$D25=\frac{1}{7}$ largest effective wellbore diameter (17)

$D10>$smallest effective wellbore diameter (18)

For example, the bridging criteria relies on the results from Equations (5)-(12) as follows: for the input flow rate (q) and its corresponding velocity, Equations (5)-(12) will determine the range of effective diameters ($d_s$) of rock fragments that will settle down. This range will constitute the particle size distribution (PSD) of deposited or settled down rock fragments. The D-values from this PSD can then be used into the applicable bridging criterion. If the different D-values from this PSD satisfy Equations (13)-(18), then the computer system 116 determines that the Vickers criterion is satisfied and that bridging, and therefore, blockage, is expected to occur.

In some implementations, the computer system 116 determines the probability that at least one restriction will occur using the Aramco criterion by evaluating the following expressions:

$D90$=largest effective wellbore diameter (sub-criterion 9) (19)

$D80$=70% mean effective wellbore diameter (sub-criterion 8) (20)

$D70$=60% mean effective wellbore diameter (sub-criterion 7) (21)

$D60$=50% mean effective wellbore diameter (sub-criterion 6) (22)

$D50$=40% mean effective wellbore diameter (sub-criterion 5) (23)

$D40$=30% mean effective wellbore diameter (sub-criterion 4) (24)

$D30$=20% mean effective wellbore diameter (sub-criterion 3) (25)

$D20$=10% mean effective wellbore diameter (sub-criterion 2) (26)

$D10>$smallest effective wellbore diameter (sub-criterion 1) (27)

For example, the bridging criteria relies on the results from Equations (5)-(12) as follows: for the input flow rate (q) and its corresponding velocity, Equations (5)-(12) will determine the range of effective diameters ($d_s$) of rock fragments that will settle down. This range will constitute the particle size distribution (PSD) of deposited or settled down rock fragments. The D-values from this PSD can then be used into the applicable bridging criterion. If the different D-values from this PSD satisfy Equations (19)-(27), then the computer system 116 determines that the Aramco criterion is satisfied and that bridging, and therefore, blockage, is expected to occur.

At block 246, the computer system 116 notifies an engineer of the probability that at least one restriction will develop in the wellbore. In some implementations, the computer system 116 notifies an engineer of the time (t), the wellbore measured depth (MD), the wellbore diameter (d), and the flow rate (q) associated with the at least one restriction.

For example, if the selected bridging criterion is satisfied, the computer system 116 issues a prediction of a restriction/blockage. In response, engineers can manipulate one or more variables that influence the probability that at least one restriction will develop. For example, engineers can change the production/injection fluid density ($\rho_f$), the flow rate (q), the slip velocity ($V_{sl}$), the rock properties, the earth in-situ stresses, and re-compute the probability that at least one restriction will develop to assess which variables must change in order to ensure that the bridging criterion is no longer satisfied. For example, engineers can lower or increase the flow rate (q) to ensure no restrictions will take place.

In some implementations, the computer system 116 determines the probability that at least one restriction will develop in the wellbore for each value of time (t), wellbore measured depth (MD), wellbore diameter (d), and flow rate (q) and presents table of probabilities to an engineer so the engineer can adjust aspects of the wellbore to reduce the probability that at least one restriction will develop. In some examples, the engineer can select a perforated cased wellbore or a wellbore with sand screens rather than an open-hole wellbore to reduce the probability that at least one restriction will develop. For example, the wellbore 102 shown in FIG. 1 has an open-hole completion setup.

In some implementations, the computer system 116 repeats the processes described with reference to FIG. 9 by varying one or more parameters at a time to determine a set of parameters that result in a low probability that at least one restriction will develop. For example, the computer system 116 repeats the process described with reference to FIG. 9 by looping over: (a) every wellbore diameter seen in caliper log measurements; (b) every production or injection rate; and (c) every point in time along with its corresponding failed rock fragments dimensions.

The processes described with reference to FIG. 9 are further explained with reference to the following example applications.

Figure 11:
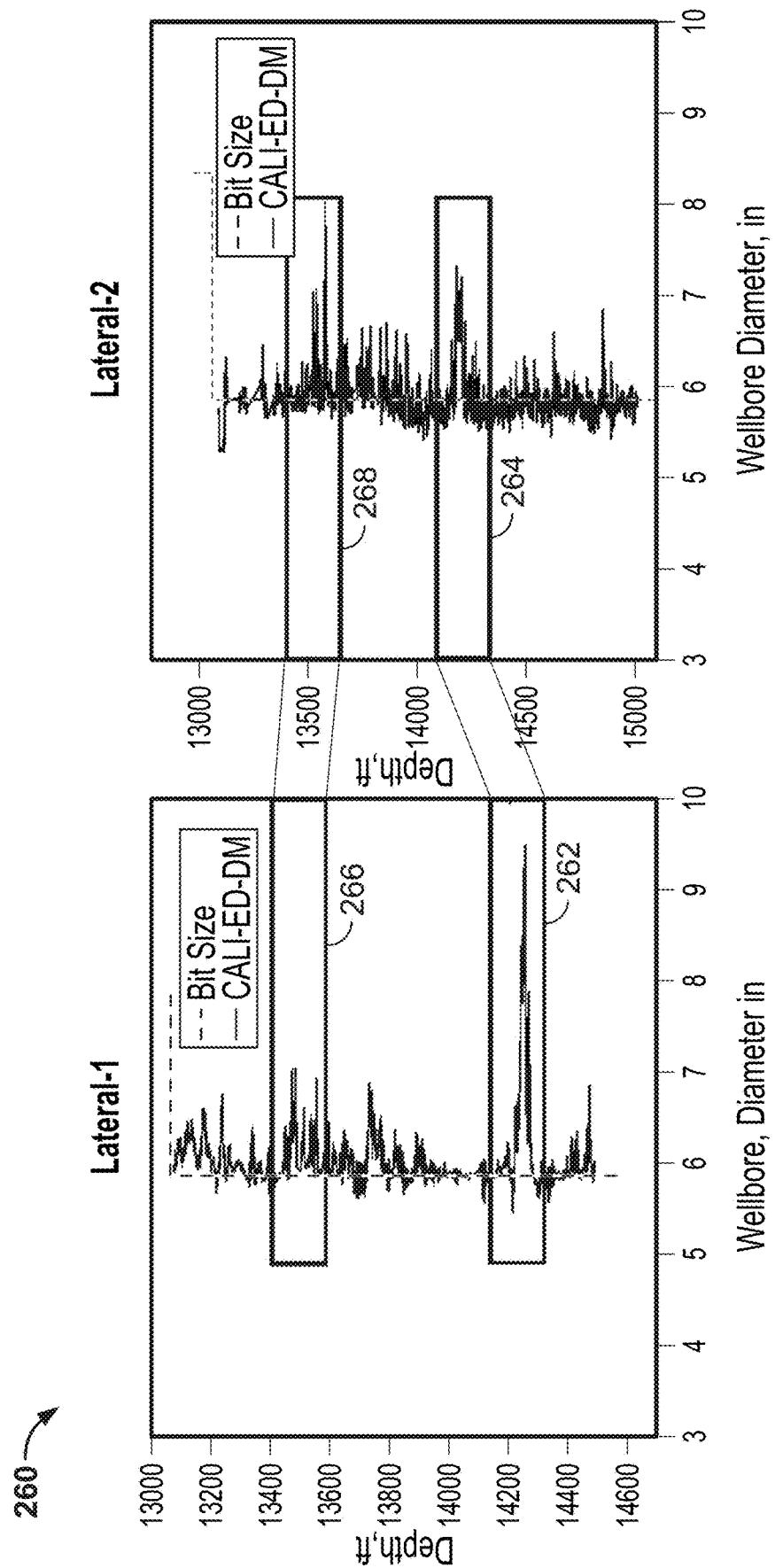
FIG. 11 is a plot of data measured from two laterals of a wellbore illustrating the presence of at least two cavings in the formation.

Application #1: Time-Dependent Sanding Tendencies with Depletion and Loading History Considerations FIG. 11 is a plot 260 of data measured from two laterals of a wellbore. The data indicates a presence of at least two cavings in the formation which is evident in windows 262, 264, 266, and 268. FIG. 11 illustrates a variation in the wellbore diameter (for example, the flow path size) due to enlargements, tights spots, and in-gauge sections. In plot 260, wireline logs from the wellbore section of interest are used to define input conditions and model parameters for the three-dimensional finite element model 162. For example, the wireline logs are used to estimate the rock mechanical properties.

As shown in plot 260, weak zones that are susceptible to wellbore stability and failure issues are identified in windows 262, 264, 266, and 268. The caliper logs generally show substantial enlargement weak zones. The enlargements can present themselves in different laterals within the same well as shown in FIG. 11.

Due to the presence of wellbore enlargements along these zones, the wireline log readings in these intervals and the mechanical properties calculated based on the wireline log data can contain quality issues and inaccuracies. To account for these issue and to account for the heterogeneous nature of the formation of interest to be measured, measurements of mechanical properties from nearby wells can be relied upon. For example, the computer system 116 can measure formation properties from one or more wells surrounding the wellbore of interest. In some examples, the cores samples are extracted from the formation and measured in a lab setting to determine one or more properties of the formation.

Figure 12A:
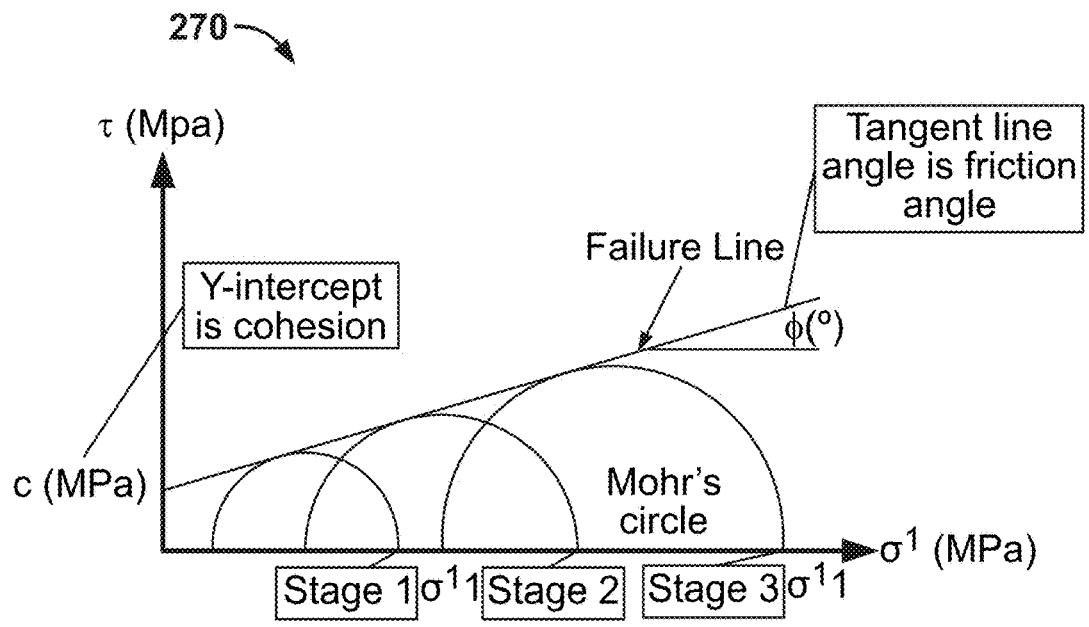
FIGS. 12A and 12B are plots used to determine one or more properties and/or a failure criterion of the formation.

FIG. 12A is a plot 270 used to determine one or more properties of the formation. For example, cohesion and friction angle of the formation are deduced from plot 270.

Figure 12B:
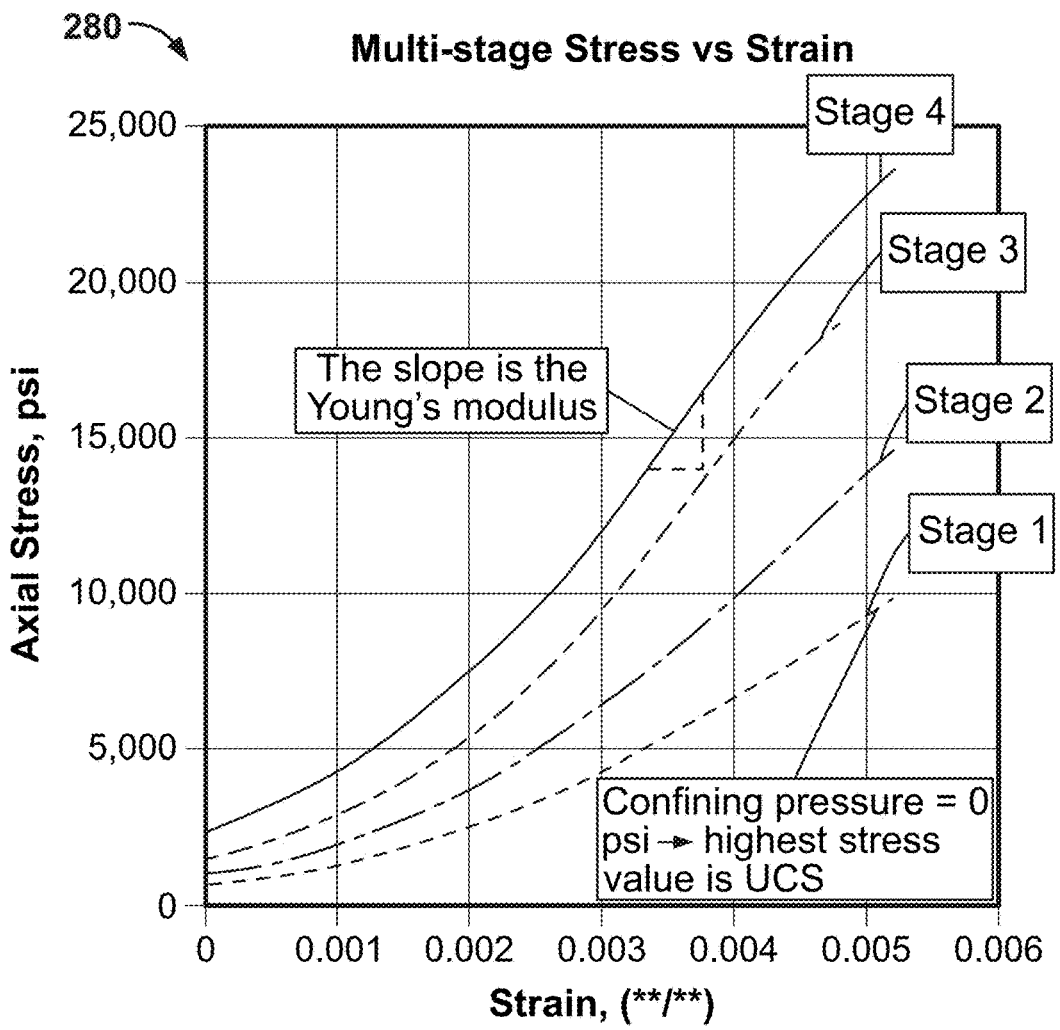

The different stages refer to increasing stages of confining pressure. FIG. 12B is a plot 280 used to determine one or more properties of the formation and/or a failure criterion of the formation.

Figure 13:
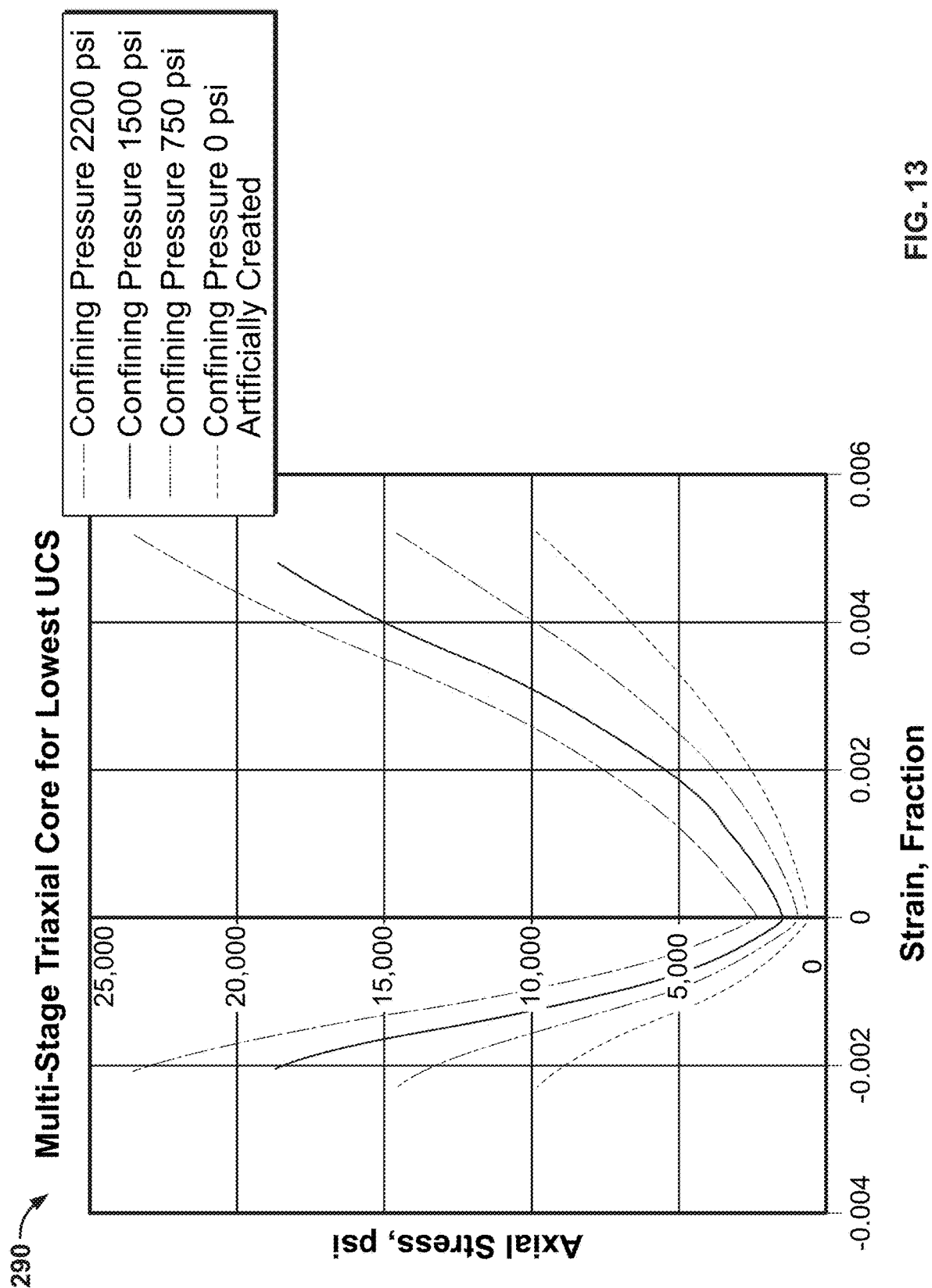
FIG. 13 is a plot of the ultimate compression strength of a formation based on confining pressures of the formation.

FIG. 13 is a plot 290 of the ultimate compressive strength of a formation based on confining pressure values created by adjacent rocks. The stress-strain curves shown in plot 290 are obtained from a multi-stage test of a core sample. The curve with zero confining pressure, which is artificially created, represents the lowest unconfined compressive strength (USC) of this formation. For example, the USC value is based on the available core measurements. In some examples, rock failure envelopes, linear elastic properties, nonlinearity coefficients, and plasticity parameters are estimated from the stress-strain curves shown in FIGS. 12A, 12B, and 13.

In some implementations, the unconfined stress-strain curve is artificially created to fit within the extrapolated UCS value from the multi-stage test. The interpretations from these curves allow for modeling the non-linear elasto-plastic behavior for following three failure criteria: (1) the Mohr-Coulomb failure criteria; (2) the Mogi-Coulomb failure criterion; and (3) the Modified Drucker-Prager failure criteria (the Lade k-value modification) as described with reference to FIG. 7. The stress-strain curves shown in plot 290 allow for a more accurate description of the deformation behavior of the rock compared to an estimation of Young's modulus and Poisson's ratio alone.

The stress and loading data for the well of interest are measured or estimated from several sources (for example, extracted cores, geological maps, seismic surveys, downhole monitoring tools, etc.). In some implementations, the input data shown in Table 2 is used as input conditions or parameters for the finite element model 162. In Table 2, "1-D MEM" refers to one-dimensional mechanical earth model.

TABLE 2

Three-dimensional finite element model input data.

| Input Data Type | Data Value | Data Source |
|---|---|---|
| Initial drilling mud weight (LT-0 only) | 102 pcf | Drilling reports |
| Final drilling mud weight (both laterals) | 79 pcf | Drilling reports |

TABLE 2-continued

Three-dimensional finite element model input data.

| Input Data Type | Data Value | Data Source |
|---|---|---|
| Completion fluid (Diesel) | 54 pcf | Drilling reports |
| Vertical in-situ stress magnitude SV | 1.1 psi/ft | 1-D MEM |
| Minimum horizontal in-situ stress magnitude SHmin | 0.86 psi/ft | 1-D MEM |
| Maximum horizontal in-situ stress magnitude SHmax | 1.15 psi/ft | 1-D MEM |
| Minimum horizontal in-situ stress direction | 0°N | Regional estimation |
| Wellbore Bit Diameter | 5⅞ inch | Wellbore Profile |
| Wellbore Azimuth | 105° | Directional survey |
| Wellbore Inclination | 90° | Directional Survey |

Variations of two variables over time are reflected in the three-dimensional finite element simulation results to account for a time-dependency in the finite element model. These variables are pore pressure and loading history. Pore pressure and loading history are used because these are the two main input variables that actually experience change over time. Pore pressure changes over time due to hydrocarbon production, injection, or invasion from wellbore fluids. Loading history changes over time due to the different operation performed on a well, which can include hydraulic fracturing, acidizing, and pressure cycling while drilling. In some examples, no other variables change over time. An example of pore pressure measurements and changes over time are shown in Table 3, where PP1, PP2, etc. represent distinct pore pressure data points.

TABLE 3

Pore pressure changes over time in the well of interest.

| Year | Pore Pressure, psi/ft |
|---|---|
| 2011 | PP1 |
| 2015 | PP2 |
| 2016 | PP3 |
| 2018 | PP4 |
| 2019 | PP5 |
| 2020 | PP6 |

As noted above, the second variable considered for time-dependent failure is loading history. Wellbore rock are subjected to different loads starting with the drilling mud weight, completion fluids, and stimulation jobs. An example of loading history data is shown in Table 4.

TABLE 4

Drilling and completion fluids history for both laterals in the well of interest.

| Mud Date | Mud Type | Mud Weight, pcf | TVD, ft | MD, ft | Days Since Spud Day | Lateral |
|---|---|---|---|---|---|---|
| Dec. 3, 2010 | POLY | 102 | 11336.47 | 11339 | 34.83 | 0 |
| Dec. 4, 2010 | POLY | 102 | 11768.67 | 11814 | 35.83 | 0 |
| Dec. 5, 2010 | POLY | 102 | 11892.57 | 11970 | 36.83 | 0 |
| Dec. 6, 2010 | POLY | 102 | 12148.12 | 12342 | 37.83 | 0 |
| Dec. 7, 2010 | POLY | 102 | 12320.54 | 12680 | 38.83 | 0 |
| Dec. 8, 2010 | POLY | 102 | 12324.84 | 12690 | 39.83 | 0 |
| Dec. 9, 2010 | POLY | 102 | 12433.18 | 13030 | 40.83 | 0 |
| Dec. 14, 2010 | POLY | 102 | 12441.47 | 13060 | 45.83 | 0 |
| Dec. 15, 2010 | POLY | 102 | 12443.79 | 13070 | 46.83 | 0 |
| Dec. 16, 2010 | POLY | 78 | 12468.76 | 13180 | 47.83 | 0 |
| Dec. 17, 2010 | CACL | 78 | 12480.79 | 13280 | 48.83 | 0 |
| Dec. 18, 2010 | NACLPOL | 78 | 12515 | 13614 | 49.83 | 0 |
| Dec. 19, 2010 | NACLPOL | 79 | 12526.1 | 14230 | 50.83 | 0 |
| Dec. 25, 2010 | NACLPOL | 79 | 12539.5 | 14610 | 56.83 | 0 |
| Dec. 26, 2010 | NACLPOL | 79 | 12461.48 | 13146 | 57.83 | 1 |

TABLE 4-continued

Drilling and completion fluids history for both laterals in the well of interest.

| Mud Date | Mud Type | Mud Weight, pcf | TVD, ft | MD, ft | Days Since Spud Day | Lateral |
|---|---|---|---|---|---|---|
| Dec. 29, 2010 | NACLPOL | 79 | 12482.31 | 13301 | 60.83 | 1 |
| Dec. 30, 2010 | NACLPOL | 79 | 12491.89 | 13410 | 61.83 | 1 |
| Dec. 31, 2010 | NACLPOL | 79 | 12521.34 | 13900 | 62.83 | 1 |
| Jan. 1, 2011 | NACLPOL | 79 | 12532.29 | 14425 | 63.83 | 1 |
| Jan. 2, 2011 | NACLPOL | 79 | 12545 | 14945 | 64.83 | 1 |
| Jan. 3, 2011 | NACLPOL | 79 | 12550 | 15090 | 65.83 | 1 |
| Jan. 8, 2011 | BRINE | 80 | 12550 | 15090 | 70.83 | 1 |
| Jan. 9, 2011 | CACL | 80 | 12550 | 15090 | 71.83 | 1 |
| Jan. 11, 2011 | DSEL | 54 | 12550 | 15090 | 73.83 | 1 |

The information of Tables 3 and 4 is used to create different simulation cases. For example, the information is used to create the different simulation cases as shown in Table 5.

TABLE 5

Description of simulation cases designed to assess time dependent failure based on the history and data of the well of interest.

| Case# | Drilling Mud Weight, pcf | Time (Yrs.) | Pore Pressure, psi/ft |
|---|---|---|---|
| 1 | 102 | 2011 | PP1 |
| 2 | | 2015 | PP2 |
| 3 | | 2016 | PP3 |
| 4 | | 2018 | PP4 |
| 5 | | 2019 | PP5 |
| 6 | | 2020 | PP6 |
| 7 | 79 | 2011 | PP1 |
| 8 | | 2015 | PP2 |
| 9 | | 2016 | PP3 |
| 10 | | 2018 | PP4 |
| 11 | | 2019 | PP5 |
| 12 | | 2020 | PP6 |

Figure 14A:
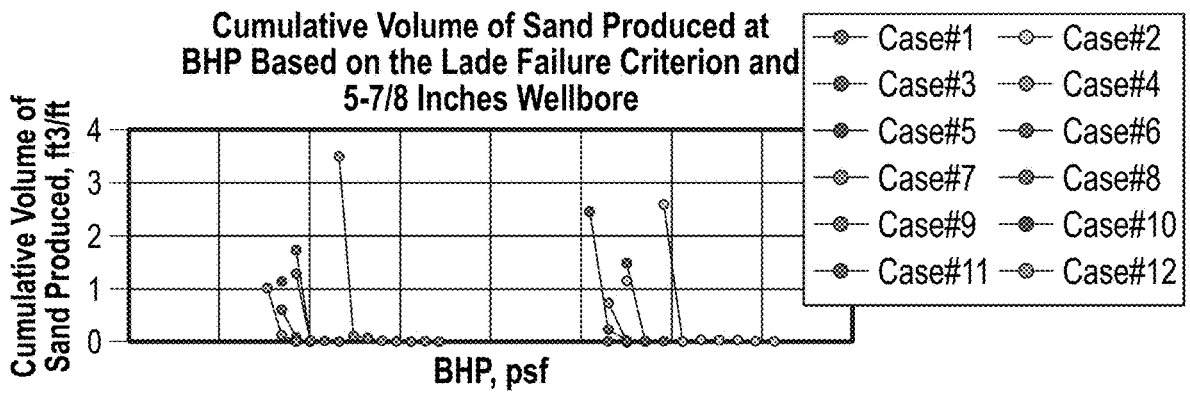
FIGS. 14A-14C are plots of the cumulative volume of sand produced at the bottom hole pressure based on various failure criterions for a 5⅞ inch diameter wellbore.
Figure 14B:
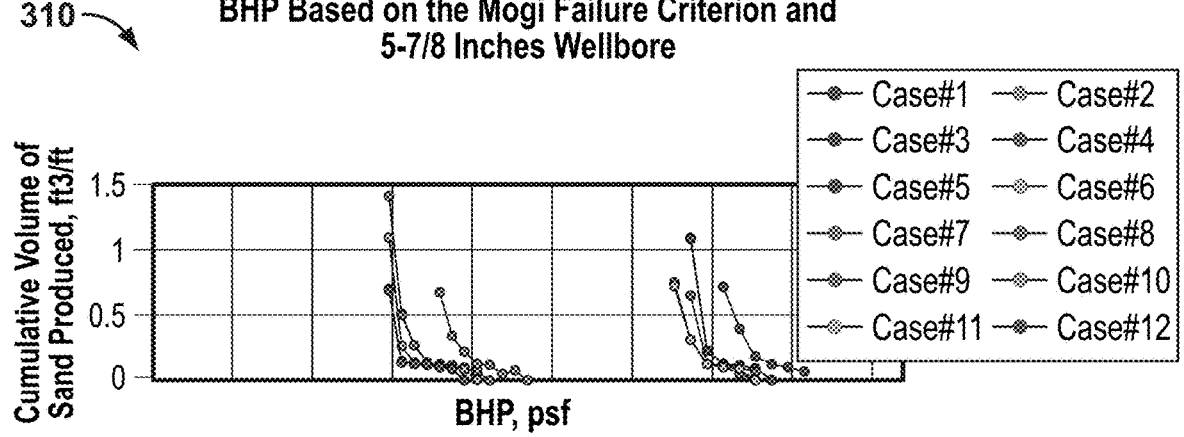
Figure 14C:
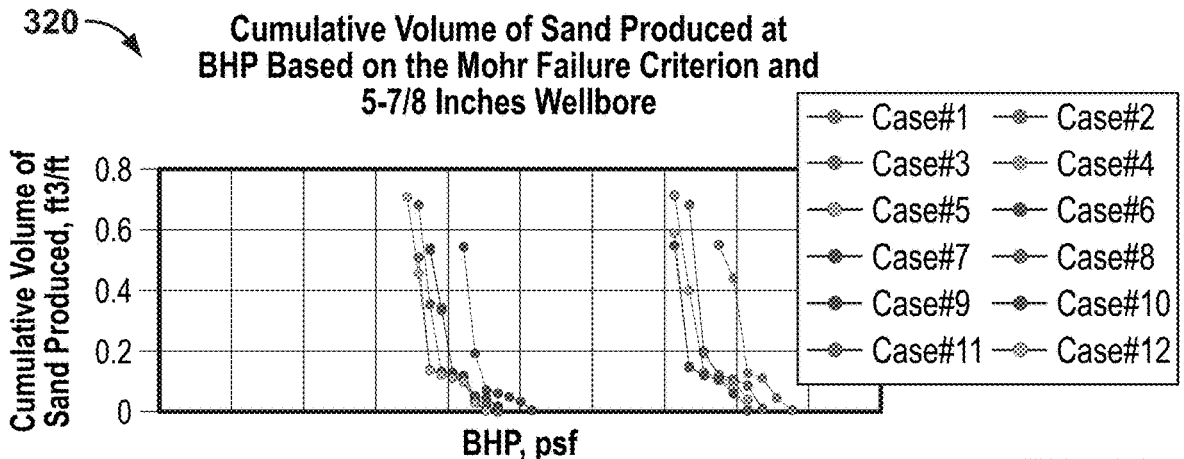
Figure 15A:
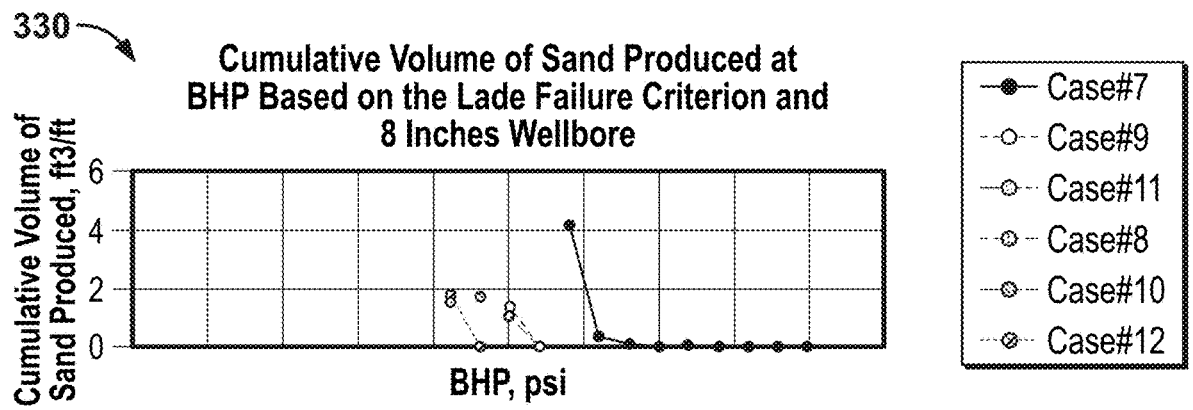
FIGS. 15A-C are plots of the cumulative volume of sand produced at the bottom hole pressure based on various failure criterions for an 8 inch diameter wellbore.
Figure 15B:
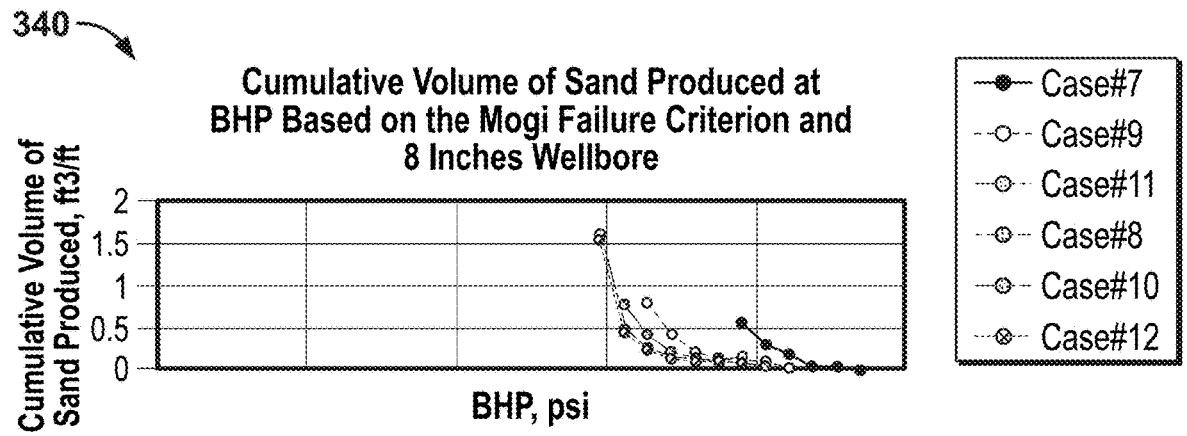
Figure 15C:
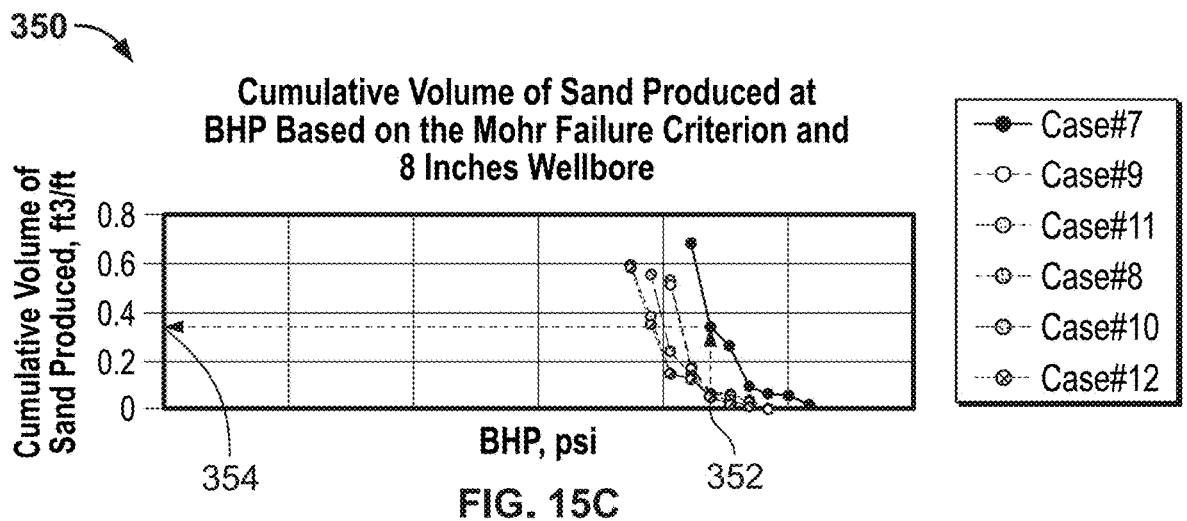

FIGS. 14A-C and 15A-C are plots of results of the cumulative volume of sand produced at bottom-hole pressures (BHP). FIG. 14A is a plot 300 of the cumulative volume of sand produced at various BHPs based on the Lade Failure Criterion for a 5⅞ inch diameter wellbore. The BHP scale is normalized and the vertical axis represents volume of sand produced per foot of the wellbore. FIG. 14B is a plot 310 of the cumulative volume of sand produced at various BHPs based on the Mogi Failure Criterion for a 5⅞ inch diameter wellbore. FIG. 14C is a plot 320 of the cumulative volume of sand produced at various BHPs based on the Mohr Failure Criterion for a 5⅞ inch diameter wellbore. FIG. 15A is a plot 330 of the cumulative volume of sand produced at various BHPs based on the Lade Failure Criterion for an 8 inch diameter wellbore. FIG. 15B is a plot 340 of the cumulative volume of sand produced at various BHPs based on the Mogi Failure Criterion for an 8 inch diameter wellbore. FIG. 15C is a plot 350 of the cumulative volume of sand produced at various BHPs based on the Mohr Failure Criterion for a 8 inch diameter wellbore.

These figures show predictions of cumulative sand (or volume failed rock fragments produced) at different bottom-hole pressure values. Since the bottom-hole pressures are controlled by different dynamic parameters such as flow rate, surface pressure, friction losses, and fluid density, the results of the simulation guide the decision-making process to ensure that sand production is minimized in the wellbore.

The computer system 116 interprets the results shown in these figures as follows. For example, consider the plot 350 of FIG. 15C and assume that the year is 2011 (Case #7) where the pore pressure is still at its initial value (PP1 from Table 2). The bottom-hole pressure (BHP) is a value that is controllable through the density of the fluid occupying the wellbore and the fluid flow rate. Assuming that the BHP in specific conditions (again due to fluid density and flow rate) is set at the value at marker 352. This means that the computer system 116 predicts that the volume of the produced sand (or failed rock fragments) will be around 3.5 $ft^3/ft$ of the wellbore.

In some examples, based on the results related to loading history, mud weights for future wells can be selected to ensure the mud weights will minimize wellbore failure throughout the production and injection periods. Mud weights is further described with reference to FIGS. 16A and 16B. In some examples, these simulation results can be used to prepare for mitigation practices to counter the sand production in surface pipelines and facilities. In some examples, these results help determine when downhole intervention is necessary to prevent impending production blockage.

Application #2: Completion Setup Selection

In this application, the computer system 116 determines a completion setup based on the sand production and the probability that at least one restriction will form in the wellbore. Generally, this analysis is performed in the pre-drilling or pre-completion phase of the wellbore so that the results can guide engineers to an adequate completion setup. The computer system 166 and the engineers will be able to make an informed decision on the optimal completion type in terms of efficiency and cost.

For example, suppose simulation results for all relevant scenarios show minimal probability of wellbore failure. In such a case, engineers will be justified to opt for the more cost-effective choice of an open-hole completion. On the other hand, if results show a medium probability of wellbore failure, engineers can opt for a safer option such as an open-hole with a gravel pack completion. Finally, in cases with a high probability of severe failure, cased and perforated completion might be justified despite a higher cost. In general, the values for "minimal" probability," "medium probability," and "high probability," vary well-to-well based on a tolerance of subsurface tubulars, surface tubulars, and surface equipment exposed to the abrasive nature of the flowing produced sand. In some examples, these values also depend on the desired production or injection rate. This is because with higher rates, the sand abrasiveness increases. In some examples, the computer system 116 presents a probability based on information from previous simulations.

In some examples, the computer system 116 associates a minimal probability with a less than 25% probability that at least one restriction will occur. In some examples, the computer system 116 associates a medium probability with between a 25% and a 75% probability that at least one restriction will occur. In some examples, the computer system 116 associates a high probability with a greater than 75% probability that at least one restriction will occur.

In some implementations, the computer system 116 determines the completion setup for the engineers. For example, the computer system 116 proposes a completion setup to the engineers to minimize cost and installation complexity while minimizing the likelihood that at least one restrictions will develop in the wellbore.

Application #3: Hole Cleaning Efficiency

The systems and methods described in this disclosure account for particle transport in a flowing fluid within a wellbore. This application relates to hole cleaning while drilling. For example, the systems account for larger rock fragments that fail off the sides of the wellbore wall, somewhat independently of the drill bit, to determine whether a wellbore should be cleaned.

Application #4: Mud Weight Windows

Figure 16A:
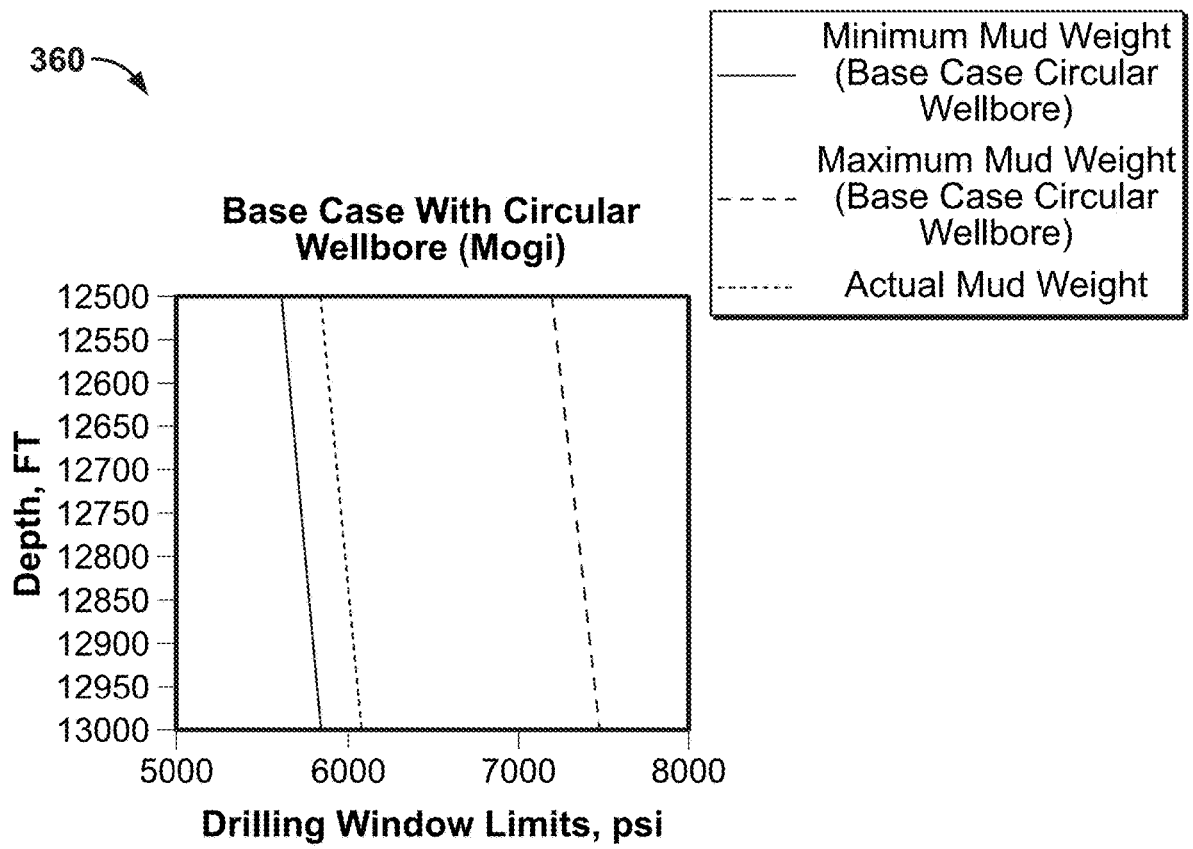
FIGS. 16A and 16B are plots 360, 370 of mud weight windows as a function of wellbore depth.
Figure 16B:
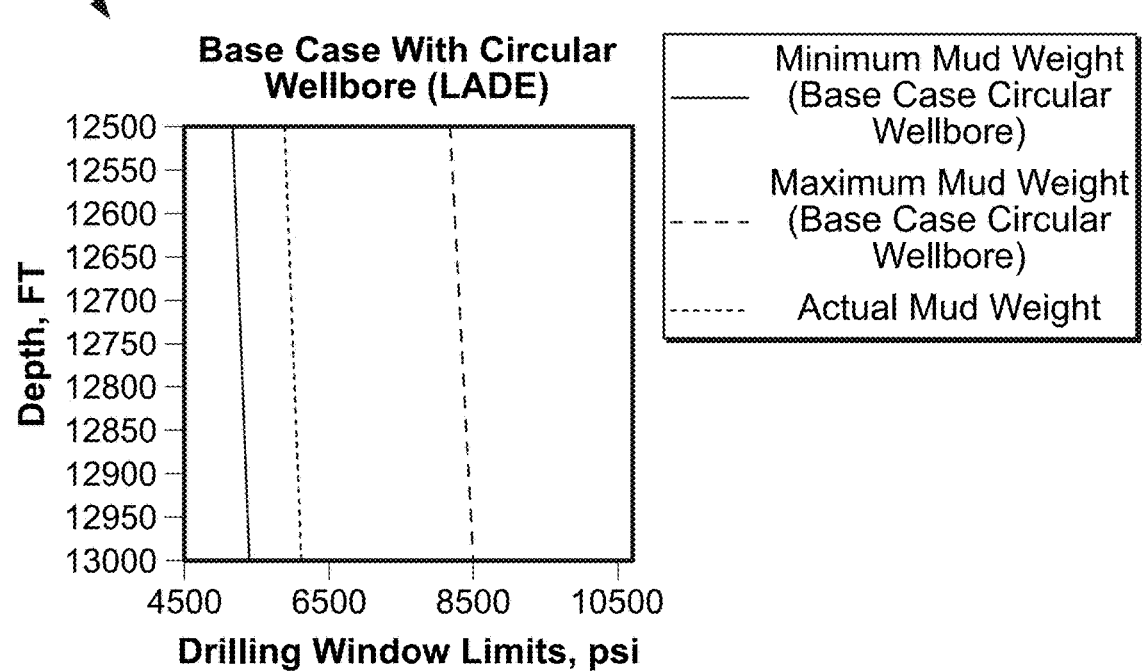

FIGS. 16A and 16B are plots 360, 370 of mud weight windows as a function of wellbore depth. In this application, the finite element model is used to determine several parameters relating to an overall collapse in the wellbore. In some examples, these parameters include the mud weight or the downhole pressure required to prevent wellbore failure. An example of the initial output of the model, which relates to recommending mud weights for preventing wellbore rock failure is shown in FIGS. 16A and 16B. In such an example, the computer system 116 determines recommendations of mud weights and/or downhole pressures required to prevent wellbore rock failure based on the results of the finite element model 162.

Figure 17:
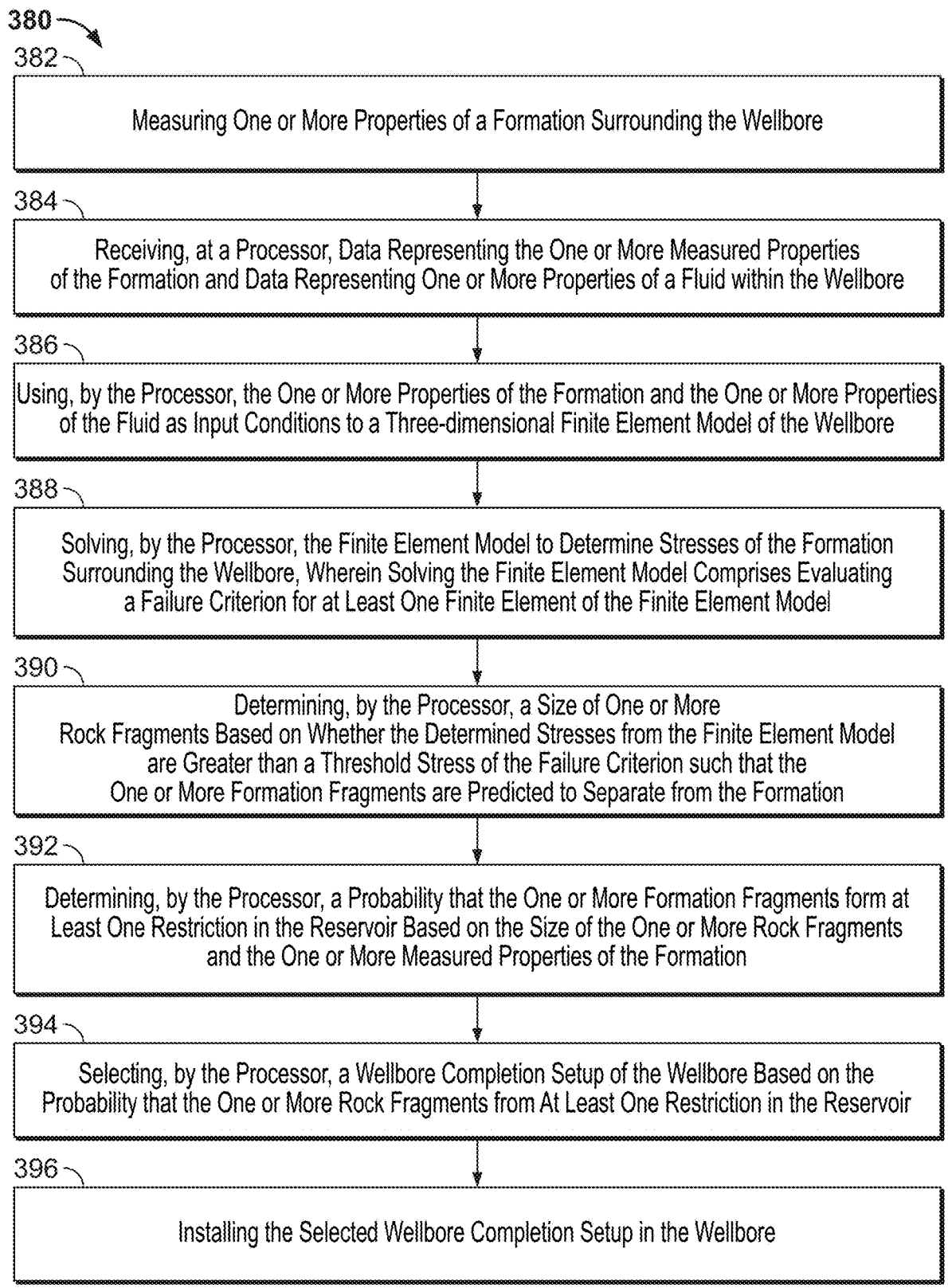
FIG. 17 is a flow chart of a method for selection and installation of a wellbore completion setup.

FIG. 17 is a flow chart 380 of a method for selection and installation of a wellbore completion setup. In some examples, one or more steps of the flow chart 380 are performed by the computer system 116 (for example, by one or more processors of the computer system 116).

At block 382, a wire log measures one or more properties of a formation surrounding the wellbore. For example, the well logging tool 148 measures a diameter of the wellbore 102. In some examples, the wire log is a caliper log and the caliper log measures the diameter of the wellbore 102 as a function of depth in the wellbore 102. In some examples, the one or more properties include (i) a density of the formation, (ii) an elastic modulus of the formation, (iii) a compressive strength of the formation, and/or (iv) pore pressures within the wellbore 102.

In some examples, the wire log measures at least two pore pressures in the wellbore 102. In some examples, a core sample is extracted from the formation and the compressive strength of the formation is determined based on a result from a compression strength test. In some examples, the wellbore includes at least two laterals and measuring the diameter of the wellbore as the function of depth within the wellbore includes measuring the diameter of the wellbore as the function of depth within each of the at least two laterals of the wellbore.

In some examples, the wire log measures one or more properties of a fluid within the wellbore. For example, the well logging tool 148 measures a density of oil 114 within the wellbore and/or within the reservoir surrounding the wellbore. In some examples, the one or more properties of the fluid include a fluid density, a fluid viscosity, a volumetric flow rate, and/or a mud weight. In some examples, the well logging tool 148 measures at least two mud weights.

At block 384, a processor (for example, a processor of the computer system 116) receives data representing the one or more measured properties of the formation and data representing one or more properties of a fluid within the wellbore. For example, the data from the well logging tool 148 is stored on a storage medium which is in electrical communication with a processor of the computer system 116.

At block 366, the processor uses the one or more properties of the formation and the one or more properties of the fluid as input conditions to a three-dimensional finite element model of the wellbore. For example, an engineer prepares a three-dimensional finite element model (for example, the finite element model 162) of the wellbore 102 and uses a density of the formation and a diameter of the wellbore as an input condition to the finite element model 162 along with a density and a volumetric flow rate of the oil 114 within the wellbore 102.

At block 368, the processor solves the finite element model to determine stresses of the formation. For example, the processor solves the finite element model 162 based on the equilibrium condition of Equation (1). The results of the solved finite element model 162 include stresses of each finite element within the finite element model 162. In some examples, the stresses spatially vary around the circumference of the wellbore and spatially vary along a depth of the wellbore. In some examples, the stress vary with respect to time.

In some implementations, the processor solves the finite element model to determine stresses of the formation by solving the finite element model for at least two mud weights and at least two pore pressures to determine stresses of the formation for at least four cases. For example, the finite element model 162 is solved to determine mud weights as described with reference to FIGS. 16A and 16B.

In some implementations, the processor evaluates a failure criterion for at least one finite element of the finite element model. For example, the processor evaluates a Mogi-Coulomb failure criterion, a Mohr-Coulomb failure criterion, and/or a Lade/Drucker-Prager failure criterion as described with reference to FIG. 7. In some implementations, the processor evaluates a failure criterion for at least one finite element of the finite element model by implementing the steps described with reference to the flow chart 190 of FIG. 7.

In some implementations, one or more parameters of the failure criterion are based on the determined compressive strength of the formation. In some implementations, the finite element model includes at least one plasticity model and solving the finite element model includes determining the stresses of the formation based on the at least one plasticity model while being subject to the failure criterion.

At block 390, the processor determines a size of one or more rock fragments based on whether the determined stresses from the finite element model are greater than a threshold stress of the failure criterion. In some examples, the determined stresses from the finite element model being greater than a threshold stress of the failure criterion indicates that one or more rock fragments are predicted to become separated from the formation. For example, the stress state surrounding the wellbore 102 can include regions 126 as described with reference to FIG. 2A. In some cases, the stresses in these regions 126 exceed the threshold stresses of the failure criterion (for example, the compressive strength and/or the tensile strength of the rock). When this occurs, one or more rock fragments 116 as described with reference to FIG. 1 are predicted to form and separate from the surrounding formation. In some examples, the processor determines a size of the rock fragments to include an effective diameter of the rock fragments.

In some implementations, the processor determines one or more regions of the formation from the numerical model where the determined stresses exceed the threshold stress. For example, as described with reference to FIGS. 8A and 8B, the processor can determine one or more regions 204A-204E where rock fragments are expected to develop based on the predicted stresses in the finite elements 202 of the regions. In some examples, each region is defined by a contiguous set of finite elements and/or nodes of the finite elements.

In some implementations, the processor determines the size of the one or more rock fragments by determining a size for each of the one or more regions of the formation where the determined stresses exceed the threshold stress. For example, the processor determines an effective diameter or volume for each region 204A-204E.

In some implementations, the processor determines the size for each of the one or more regions of the formation by retrieving one or more coordinates of each node of the finite element model where the stresses exceed the threshold stress. For example, as described with reference to FIGS. 8A and 8B, the processor executes a convex hull algorithm to trace the boundary of each region.

In some implementations, the processor determines the size for each of the one or more regions of the formation by (i) determining a polygon that encapsulates each of the one or more coordinates of each node of the finite element model where the stresses exceed the threshold stress, (ii) determining the size of the one or more rock fragments based on one or more dimensions of the determined polygon, and (ii) determining the diameter of the wellbore based on a size of the determined polygon.

In some implementations, the processor determines the size of one or more rock fragments based on the determined size of one or more regions. In some examples, the size of the rock fragments substantially corresponds to the size of the regions.

In some implementations, the processor uses at least one result of the finite element model to determine a predicted diameter of the wellbore as a function of depth within the wellbore based on the determined size of the one or more rock fragments. In some implementations, the processor compares the measured diameter of the wellbore to the predicted diameter of the wellbore to validate the finite element model.

At block 392, the processor determines a probability that the one or more rock fragments form at least one restriction in a reservoir based on the size of the one or more rock fragments and the one or more measured properties of the formation. For example, if the measured diameter of the wellbore is less than the effective diameter of one or more rock fragments, the processor determines that at least one restriction is likely to occur. In these examples, the probability is determined by comparing the diameters of each of the one or more rock fragments from the finite element model to the measured diameter of the wellbore.

In some implementations, the processor determines a mean or maximum diameter of the wellbore based on the measured diameter of the wellbore. The measured diameter of the wellbore represents the diameter of the wellbore as a function of depth within the wellbore. In some implementations, comparing the predicted diameters from the finite element model to the measured diameter includes comparing the diameters from the finite element model to the determined mean or maximum diameter of the wellbore.

In some implementations, the processor determines a statistical distribution of the effective diameters of the one or more rock fragments based on the determined effective diameters of each of the one or more rock fragments from the finite element model. In some implementations, the processor compares the statistical distribution of the effective diameters of the one or more rock fragments to the measured diameter of the wellbore. For example, the processor determines a normal distribution of the effective diameters. In some examples, the processor determines a lower quartile effective diameter, and upper quartile effective diameter, a mean effective diameter, and a median effective diameter based on a normal statistical distribution of the effective diameters within the wellbore.

In some implementations, the processor determines a number of occurrences within a pre-determined percentile range of the statistical distribution. For example, the processor determines a number of rock fragments that are predicted to be present with an effective diameter that corresponds with a lower quartile range. In some implementations, the processor compares the number of occurrences to the measured diameter of the wellbore.

In some implementations, the processor determines that the probability is greater than a restriction threshold when the number of occurrences within the pre-determined percentile range of the statistical distribution is greater than or equal to a pre-determined fraction of the maximum measured diameter of the wellbore. In some examples, the probability being greater than the restriction threshold is indicative that at least one restriction is likely to occur. In some examples, the processor implements the one-third rule, the Vickers criterion, and/or the Aramco criterion as described with reference to Equations (13)-(27).

In some implementations, the processor determines that the probability is less than the restriction threshold when the number of occurrences within the pre-determined percentile interval of the statistical distribution is less than the pre-determined fraction of the maximum measured diameter of the wellbore. In some examples, the probability being less than the restriction threshold is indicative that at least one restriction is unlikely to occur in the reservoir. In some examples, the processor implements the one-third rule, the Vickers criterion, and/or the Aramco criterion as described with reference to Equations (13)-(27).

In some implementations, the processor determines a flow regime of the fluid based on the one or more properties of the fluid within wellbore. For example, the computer system 116 determines a flow regime of the fluid according to the processes described with reference to blocks 226 and 232 of FIG. 9. In some examples, the processor determines the flow regime to be either turbulent or laminar based on a Reynolds number as described with reference to block 232 of FIG. 9. In some examples, the processor determines a drag coefficient of the one or more rock fragments based on the one or more properties of the fluid within wellbore and the determined flow regime. For example, the computer system 116 determines a drag coefficient based on the processes described with reference to block 230 of FIG. 9.

In some implementations, the processor determines a predicted cumulative volume of sand produced as a function of a bottom hole pressure of the wellbore based on the determined stresses from the finite element model. In some examples, the processor determines the probability based on the predicted cumulative volume of sand produced. For example, the computer system 116 implements a process to produce the plots shown in FIGS. 14A-C and 15A-C to determine the cumulative volume of sand produced as a result of the rock fragments forming in the wellbore. In some implementations, the processor determines the probability based on the predicted maximum cumulative volume of sand. For example, if the cumulative volume of sand is above a threshold (for example, 2 ft$^3$/ft), then the computer system 116 determines that at least one restrictions is likely to occur.

In some implementations, the processor determines a settling velocity of the one or more rock fragments based on one or more properties of the fluid within wellbore. For example, the computer system 116 determines the settling velocity ($V_{sl}$) as described with reference to Equations (6) and (10). In some implementations, the processor determines that the probability is greater than a restriction threshold when the determined settling velocity of the one or more rock fragments is less than a settling velocity threshold. For example, the probability being greater than the restriction threshold is indicative that at least one restriction is likely to occur in the reservoir.

In some implementations, the processor determines a height of a rock fragment bed accumulation based on a diameter of each of the one or more rock fragments, a direction of the height being perpendicular to a longitudinal axis of the wellbore. In some examples, the computer system 116 implements the bed accumulation expression of Equation (12) to determine the height of bed accumulation in the wellbore.

At block 394, the processor selects the wellbore completion setup of the wellbore based on the probability that the one or more rock fragments form at least one restriction in the reservoir. For example, the processor selects the completion setup to be an open-hole completion when the probability is less than a first threshold (for example, 25%). In some examples, the processor selects the completion setup to be an open-hole with a gravel pack completion setup when the probability is between the first threshold and a second threshold (for example, 75%). In some examples, the processor selects the completion setup to be a cased and perforated completion setup when the probability is greater the second threshold.

At block 396, the selected wellbore completion setup is installed in the wellbore. For example, an engineer installs the selected completion setup in the wellbore as part of a completion process before the well is used for production.

Figure 18:
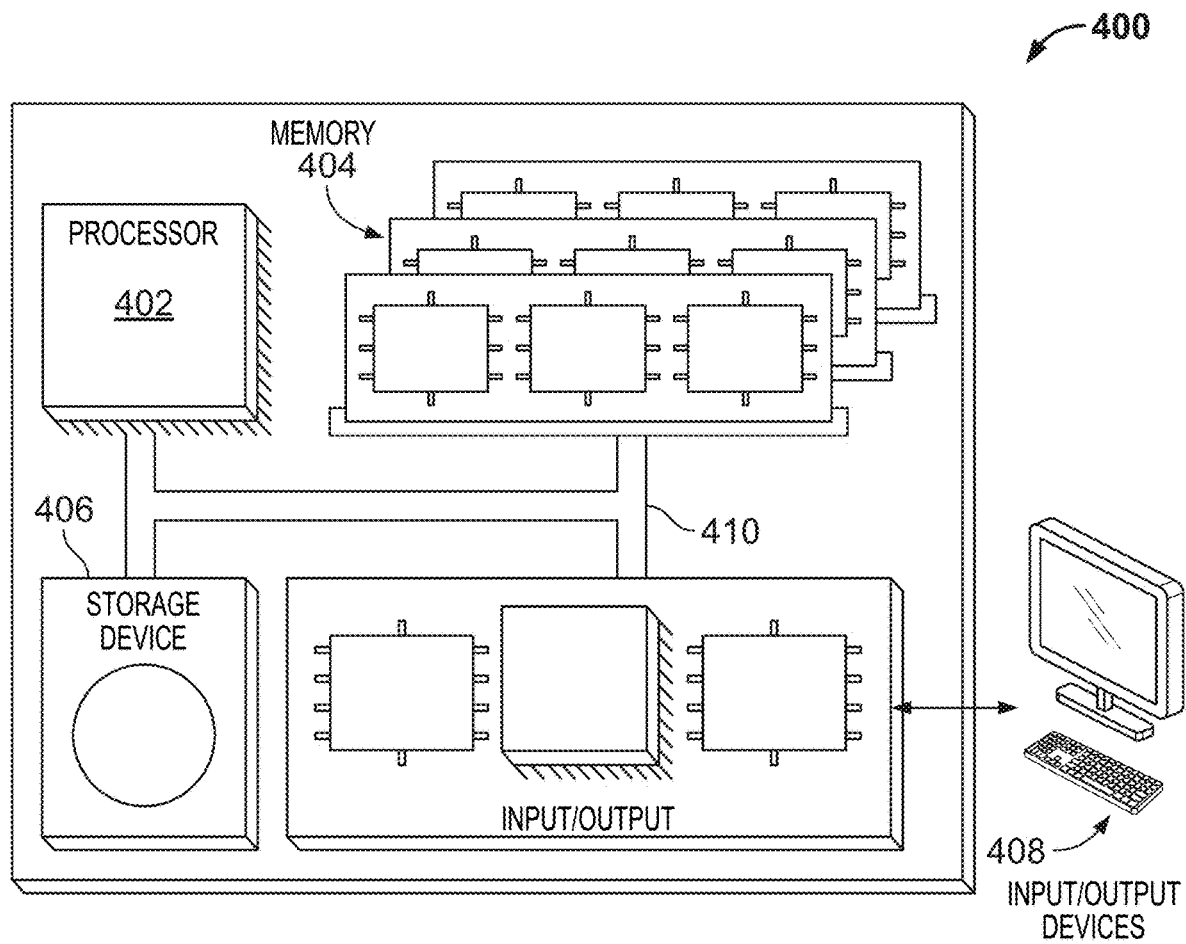
FIG. 18 is a schematic of a computer system for executing the finite element model and performing one or more steps of the systems and methods described throughout this disclosure.

FIG. 18 is a schematic of a computer 400 for executing the finite element model 162 and performing one or more steps of the systems and methods described throughout this disclosure. For example, the computer system 116 used to solve the finite element model 162 includes one or more components and features of the computer 400.

The computer 400 is intended to include various forms of digital computers, such as printed circuit boards (PCB), processors, digital circuitry, or otherwise parts of a system for determining a subterranean formation breakdown pressure. Additionally the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The computer 400 includes a processor 402, a memory 404, a storage device 406, and an input/output device 408 (for example, displays, input devices, sensors, valves, pumps, etc.). Each of the components 402, 404, 406, and 408 are interconnected using a system bus 410. The processor 402 is capable of processing instructions for execution within the computer 400. The processor may be designed using any of a number of architectures. For example, the processor 402 may be a CISC (Complex Instruction Set Computers) processor, a RISC (Reduced Instruction Set Computer) processor, or a MISC (Minimal Instruction Set Computer) processor.

In one implementation, the processor 402 is a single-threaded processor. In another implementation, the processor 402 is a multi-threaded processor. The processor 402 is capable of processing instructions stored in the memory 404 or on the storage device 406 to display graphical information for a user interface on the input/output device 408.

The memory 404 stores information within the computer 400. In one implementation, the memory 404 is a computer-readable medium. In one implementation, the memory 404 is a volatile memory unit. In another implementation, the memory 404 is a non-volatile memory unit.

The storage device 406 is capable of providing mass storage for the computer 400. In one implementation, the storage device 406 is a computer-readable medium. In various different implementations, the storage device 406 may be a floppy disk device, a hard disk device, an optical disk device, or a tape device.

The input/output device 408 provides input/output operations for the computer 400. In one implementation, the input/output device 408 includes a keyboard and/or pointing device. In another implementation, the input/output device 408 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as εPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for installing a wellbore completion setup of a wellbore, the method comprising:
    measuring one or more properties of a formation surrounding the wellbore;
    measuring one or more properties of a fluid within the wellbore;
    receiving, at a processor, data representing the one or more measured properties of the formation and data representing the one or more properties of a fluid within the wellbore;
    using, by the processor, the one or more properties of the formation and the one or more properties of the fluid as input conditions to a three-dimensional finite element model of the wellbore;
    solving, by the processor, the finite element model to determine stresses of the formation, wherein solving the finite element model comprises evaluating a failure criterion for at least one finite element of the finite element model;
    determining, by the processor, a size of one or more rock fragments based on whether the determined stresses from the finite element model are greater than a threshold stress of the failure criterion such that the one or more rock fragments are predicted to separate from the formation;
    determining, by the processor, a probability that the one or more rock fragments form at least one restriction in a reservoir based on the size of the one or more rock fragments and the one or more measured properties of the formation;
    selecting, by the processor, the wellbore completion setup of the wellbore based on the probability that the one or more rock fragments form at least one restriction in the reservoir; and
    installing the selected wellbore completion setup in the wellbore.

2. The method of claim 1, wherein measuring the one or more properties of the formation comprises measuring, using a caliper log, a diameter of the wellbore as a function of depth within the wellbore.

3. The method of claim 2, further comprising:
    determining, by the processor using at least one result of the finite element model, a predicted diameter of the wellbore as a function of depth based on the determined size of the one or more rock fragments;
    comparing the measured diameter of the wellbore to the predicted diameter of the wellbore; and
    validating, by the processor, the finite element model based on the comparison.

4. The method of claim 3, wherein the wellbore comprises at least two laterals and measuring the diameter of the wellbore as the function of depth within the wellbore comprises measuring the diameter of the wellbore as the function of depth within each of the at least two laterals of the wellbore.

5. The method of claim 1, wherein measuring the one or more properties of the formation comprises:
    extracting a core sample from the formation; and
    determining, by testing the extracted core sample, a compressive strength of the formation.

6. The method of claim 5, further comprising determining, by the processor, one or more parameters of the failure criterion based on the determined compressive strength of the formation.

7. The method of claim 1, wherein the finite element model includes at least one plasticity model and solving the finite element model comprises determining the stresses of the formation based on the at least one plasticity model while being subject to the failure criterion.

8. The method of claim 1, wherein determining the size of the one or more rock fragments comprises:
    determining, by the processor, one or more regions of the formation from the finite element model where the determined stresses exceed the threshold stress;
    determining, by the processor, a size for each of the one or more regions of the formation where the determined stresses exceed the threshold stress;
    determining the size of the one or more rock fragments based on the determined size of the one or more regions; and
    determining a diameter of the wellbore based on the determined size of the one or more regions.

9. The method of claim 8, wherein determining the size for each of the one or more regions of the formation comprises:
    retrieving one or more coordinates of each node of the finite element model where the stresses exceed the threshold stress;
    determining a polygon that encapsulates each of the one or more coordinates of each node of the finite element model where the stresses exceed the threshold stress;
    determining the size of the one or more rock fragments based on one or more dimensions of the determined polygon; and
    determining the diameter of the wellbore based on a size of the determined polygon.

10. The method of claim 1, wherein measuring the one or more properties of the formation comprises measuring, using a caliper log, a diameter of the wellbore,
    wherein determining the size of the one or more rock fragments comprises determining an effective diameter of each of the one or more rock fragments, and
    wherein determining the probability comprises determining the probability by comparing the effective diameters of each of the one or more rock fragments from the finite element model to the measured diameter of the wellbore.

11. The method of claim 10, further comprising:
    determining, by the processor, a mean diameter of the wellbore based on the measured diameter of the wellbore,
    wherein comparing the effective diameters from the finite element model to the measured diameter comprises comparing the diameters from the finite element model to the determined mean diameter of the wellbore.

12. The method of claim 10, further comprising:
    determining, by the processor, a statistical distribution of the effective diameters of the one or more rock fragments based on each of the one or more rock fragments from the finite element model,
    wherein comparing the effective diameters from the finite element model to the measured diameter comprises comparing the statistical distribution of the diameters of the one or more rock fragments to the measured diameter of the wellbore.

13. The method of claim 12, further comprising:
    determining, by the processor, a number of occurrences within a pre-determined percentile range of the statistical distribution,
    wherein comparing the statistical distribution of the effective diameters of the one or more rock fragments to the measured diameter of the wellbore comprises comparing the number of occurrences to the measured diameter of the wellbore.

14. The method of claim 13, wherein determining the probability comprises:
    determining that the probability is greater than a restriction threshold when the number of occurrences within the pre-determined percentile range of the statistical distribution is greater than or equal to a pre-determined fraction of the maximum measured diameter of the wellbore, wherein the probability being greater than the restriction threshold is indicative that at least one restriction is likely to occur; and
    determining that the probability is less than the restriction threshold when the number of occurrences within the pre-determined percentile interval of the statistical distribution is less than the pre-determined fraction of the maximum measured diameter of the wellbore, wherein the probability being less than the restriction threshold is indicative that at least one restriction is unlikely to occur.

15. The method of claim 1, further comprising:
    determining, by the processor, a settling velocity of the one or more rock fragments based on the one or more properties of the fluid within wellbore,
    wherein determining the probability comprises determining that the probability is greater than a restriction threshold when the determined settling velocity of the one or more rock fragments is less than a settling velocity threshold, wherein the probability being greater than the restriction threshold is indicative that at least one restriction is likely to occur.

16. The method of claim 1, further comprising determining a height of a rock fragment bed accumulation based on an effective diameter of each of the one or more rock fragments.

17. The method of claim 16, wherein a direction of the height is perpendicular to a longitudinal axis of the wellbore.

18. The method of claim 1, wherein determining the probability comprises:
    determining, by the processor, a flow regime of the fluid based on the one or more properties of the fluid within wellbore, the determined flow regime being either turbulent or laminar; and
    determining, by the processor, a drag coefficient of the one or more rock fragments based on the one or more properties of the fluid within wellbore and the determined flow regime.

19. The method of claim 1, wherein determining the probability comprises:
    determining a predicted cumulative volume of sand produced as a function of a bottom hole pressure of the wellbore based on the determined stresses from the finite element model; and
    determining the probability based on the predicted cumulative volume of sand produced.

20. The method of claim 1, wherein selecting the completion setup of the wellbore comprises:
    selecting the completion setup to be an open-hole completion when the probability is less than a first threshold;

selecting the completion setup to be an open-hole with a gravel pack completion setup when the probability is between the first threshold and a second threshold; and selecting the completion setup to be a cased and perforated completion setup when the probability is greater the second threshold.

* * * * *